(12) United States Patent
Berelsman et al.

(10) Patent No.: US 9,301,766 B2
(45) Date of Patent: Apr. 5, 2016

(54) APPARATUS FOR REPAIRING BONE DEFECTS

(71) Applicant: Biomet Sports Medicine, LLC, Warsaw, IN (US)

(72) Inventors: Brian K. Berelsman, Warsaw, IN (US); William Maxson, Fort Wayne, IN (US); Paul Robert, St. Catherines (CA)

(73) Assignee: BIOMET SPORTS MEDICINE, LLC, Warsaw, IN (US)

( * ) Notice: Subject to any disclaimer, the term of this patent is extended or adjusted under 35 U.S.C. 154(b) by 0 days.

(21) Appl. No.: 14/281,082

(22) Filed: May 19, 2014

(65) Prior Publication Data

US 2014/0257299 A1 Sep. 11, 2014

Related U.S. Application Data

(62) Division of application No. 13/169,075, filed on Jun. 27, 2011, now Pat. No. 8,728,084.

(51) Int. Cl.
*A61F 5/00* (2006.01)
*A61B 17/16* (2006.01)
*A61B 17/17* (2006.01)
(Continued)

(52) U.S. Cl.
CPC ......... *A61B 17/1675* (2013.01); *A61B 17/1604* (2013.01); *A61B 17/1615* (2013.01); *A61B 17/1764* (2013.01); *A61B 17/92* (2013.01); *A61F 2/30749* (2013.01); *A61B 2017/922* (2013.01); *A61B 2019/303* (2013.01);
(Continued)

(58) Field of Classification Search
CPC ........... A61B 17/1675; A61B 17/1764; A61B 17/1615; A61B 17/1604; A61B 2017/922; A61B 2019/303; A61F 2/30749; A61F 2/28; A61F 2/389; A61F 2/30756
See application file for complete search history.

(56) References Cited

U.S. PATENT DOCUMENTS 3,633,583 A 1/1972 Fishbein
4,050,100 A 9/1977 Barry
(Continued)

FOREIGN PATENT DOCUMENTS

EP 0095296 A2 11/1983
EP 0327387 A2 8/1989
(Continued)

OTHER PUBLICATIONS

FlipCutter_Arthrex-brochure_8pp_2010.
(Continued)

*Primary Examiner* — Christopher Beccia
*Assistant Examiner* — Diana S Jones
(74) *Attorney, Agent, or Firm* — Schwegman Lundberg & Woessner, P.A.

(57) ABSTRACT

A system for repairing a soft tissue or bone defect can include a C-shaped guide member having a first end and a second end and configured to extend around a condyle area of a femur of a patient. The guide member includes a threaded bore at the first end, and the second end configured to rest on a tibia of the patient. The system includes a cannulated bullet threadably received in the threaded bore and configured to be threadably advanced to secure the guide member relative to the femur. The system also includes a drilling member insertable through the bullet and configured to drill a femoral bore through the femur.

20 Claims, 17 Drawing Sheets

(51) Int. Cl.
  *A61B 17/92* (2006.01)
  *A61B 19/00* (2006.01)
  *A61F 2/30* (2006.01)
  *A61F 2/28* (2006.01)
  *A61F 2/38* (2006.01)

(52) U.S. Cl.
  CPC .............. *A61F 2/28* (2013.01); *A61F 2/30756* (2013.01); *A61F 2/389* (2013.01)

(56) References Cited

U.S. PATENT DOCUMENTS

| | | | |
|---|---|---|---|
| 4,489,446 A | 12/1984 | Reed | |
| 4,896,663 A | 1/1990 | Vandewalls | |
| 4,911,153 A | 3/1990 | Border | |
| 5,019,908 A | 5/1991 | Su | |
| D318,496 S | 7/1991 | Tse | |
| 5,030,219 A | 7/1991 | Matsen, III et al. | |
| 5,064,431 A | 11/1991 | Gilbertson et al. | |
| D325,356 S | 4/1992 | Kin Man Tse | |
| 5,129,908 A | 7/1992 | Petersen | |
| D330,371 S | 10/1992 | Tse | |
| D331,044 S | 11/1992 | Tse | |
| 5,180,384 A | 1/1993 | Mikhail | |
| D333,324 S | 2/1993 | Michael | |
| D333,848 S | 3/1993 | Tse | |
| D336,746 S | 6/1993 | Tse | |
| 5,222,955 A | 6/1993 | Mikhail | |
| D337,575 S | 7/1993 | Tse | |
| D338,331 S | 8/1993 | Kin-Man Tse | |
| 5,236,462 A | 8/1993 | Mikhail | |
| D339,759 S | 9/1993 | Ho | |
| D340,479 S | 10/1993 | Ho | |
| D341,713 S | 11/1993 | Tse | |
| 5,259,626 A | 11/1993 | Ho | |
| D342,763 S | 12/1993 | Tse | |
| 5,269,786 A | 12/1993 | Morgan | |
| D342,973 S | 1/1994 | Ho | |
| D343,210 S | 1/1994 | Tse | |
| D343,511 S | 1/1994 | Tse | |
| D343,649 S | 1/1994 | Ho | |
| D344,061 S | 2/1994 | Tse | |
| D344,107 S | 2/1994 | Tse | |
| 5,284,482 A | 2/1994 | Mikhail | |
| D344,708 S | 3/1994 | Ho | |
| D346,691 S | 5/1994 | Tse | |
| D347,247 S | 5/1994 | Ho | |
| 5,312,411 A | 5/1994 | Steele et al. | |
| D347,663 S | 6/1994 | Ho | |
| 5,324,295 A | 6/1994 | Shapiro | |
| 5,345,214 A | 9/1994 | Tsui et al. | |
| 5,350,380 A | 9/1994 | Goble et al. | |
| 5,350,383 A | 9/1994 | Schmieding et al. | |
| D352,529 S | 11/1994 | Ho | |
| D352,739 S | 11/1994 | Ho | |
| D352,970 S | 11/1994 | Ho | |
| D353,764 S | 12/1994 | Ho | |
| D354,092 S | 1/1995 | Ho | |
| 5,383,937 A | 1/1995 | Mikhail | |
| D355,450 S | 2/1995 | Ho | |
| 5,403,322 A | 4/1995 | Herzenberg et al. | |
| 5,409,494 A | 4/1995 | Morgan | |
| D357,844 S | 5/1995 | Ho | |
| D357,946 S | 5/1995 | Ho | |
| D358,761 S | 5/1995 | Ho | |
| 5,437,676 A | 8/1995 | Bouraly et al. | |
| 5,486,178 A | 1/1996 | Hodge | |
| 5,520,695 A | 5/1996 | Luckman | |
| 5,531,759 A | 7/1996 | Kensey et al. | |
| 5,554,158 A | 9/1996 | Vinciguerra et al. | |
| 5,562,664 A | 10/1996 | Durlacher et al. | |
| 5,575,794 A | 11/1996 | Walus et al. | |
| 5,580,353 A | 12/1996 | Mendes et al. | |
| 5,620,448 A | 4/1997 | Puddu | |
| 5,628,756 A | 5/1997 | Barker, Jr. et al. | |
| 5,634,927 A | 6/1997 | Houston et al. | |
| 5,648,797 A | 7/1997 | Lam | |
| 5,662,681 A | 9/1997 | Nash et al. | |
| 5,683,400 A | 11/1997 | McGuire | |
| 5,716,397 A | 2/1998 | Myers | |
| 5,741,266 A | 4/1998 | Moran et al. | |
| 5,749,875 A | 5/1998 | Puddu | |
| 5,824,066 A | 10/1998 | Gross | |
| D402,976 S | 12/1998 | Heung | |
| 5,885,297 A | 3/1999 | Matsen, III | |
| 5,906,596 A | 5/1999 | Tallarida | |
| D413,634 S | 9/1999 | Tam | |
| D413,938 S | 9/1999 | Tam | |
| D429,728 S | 8/2000 | Hays | |
| D430,569 S | 9/2000 | Hays | |
| 6,143,012 A | 11/2000 | Gausepohl | |
| 6,159,214 A | 12/2000 | Michelson | |
| 6,342,056 B1 | 1/2002 | Mac-Thiong et al. | |
| D456,813 S | 5/2002 | Hays | |
| 6,386,979 B1 | 5/2002 | Ho et al. | |
| 6,520,964 B2 | 2/2003 | Tallarida et al. | |
| 6,527,754 B1 | 3/2003 | Tallarida et al. | |
| 6,610,067 B2 | 8/2003 | Tallarida et al. | |
| 6,679,917 B2 | 1/2004 | Ek | |
| 6,716,234 B2 | 4/2004 | Grafton et al. | |
| 6,962,577 B2 | 11/2005 | Tallarida et al. | |
| 7,029,479 B2 | 4/2006 | Tallarida et al. | |
| 7,029,490 B2 | 4/2006 | Grafton et al. | |
| 7,048,754 B2 | 5/2006 | Martin et al. | |
| 7,063,717 B2 | 6/2006 | St. Pierre et al. | |
| 7,125,421 B2 | 10/2006 | Tremulis et al. | |
| 7,163,541 B2 | 1/2007 | Ek | |
| 7,238,189 B2 | 7/2007 | Schmieding et al. | |
| 7,311,702 B2 | 12/2007 | Tallarida et al. | |
| 7,510,558 B2 | 3/2009 | Tallarida et al. | |
| 7,604,641 B2 | 10/2009 | Tallarida et al. | |
| 7,618,462 B2 | 11/2009 | Ek | |
| 7,678,151 B2 | 3/2010 | Ek | |
| 7,713,251 B2 | 5/2010 | Tallarida et al. | |
| 7,713,305 B2 | 5/2010 | Ek | |
| 7,731,732 B2 | 6/2010 | Ken | |
| 7,749,250 B2 | 7/2010 | Stone et al. | |
| 7,758,611 B2 | 7/2010 | Kato | |
| 7,803,143 B2 | 9/2010 | Tallarida et al. | |
| 7,811,266 B2 | 10/2010 | Eliasen | |
| 7,828,853 B2 | 11/2010 | Ek et al. | |
| 7,857,817 B2 | 12/2010 | Tallarida et al. | |
| 7,896,883 B2 | 3/2011 | Ek et al. | |
| 7,896,885 B2 | 3/2011 | Miniaci et al. | |
| 7,896,922 B2 | 3/2011 | Engh et al. | |
| 7,901,408 B2 | 3/2011 | Ek et al. | |
| 7,914,545 B2 | 3/2011 | Ek | |
| 7,951,163 B2 | 5/2011 | Ek | |
| 8,147,559 B2 | 4/2012 | Tallarida et al. | |
| 8,177,841 B2 | 5/2012 | Ek | |
| 8,211,113 B2 | 7/2012 | Brown et al. | |
| 8,252,022 B2 | 8/2012 | Holman et al. | |
| 8,728,084 B2 | 5/2014 | Berelsman et al. | |
| 2001/0000532 A1 | 4/2001 | Michelson | |
| 2001/0041938 A1 | 11/2001 | Hein | |
| 2002/0055783 A1 | 5/2002 | Tallarida et al. | |
| 2002/0147498 A1 | 10/2002 | Tallarida et al. | |
| 2003/0060887 A1 | 3/2003 | Ek | |
| 2003/0120276 A1 | 6/2003 | Tallarida et al. | |
| 2003/0225456 A1 | 12/2003 | Ek | |
| 2004/0015170 A1 | 1/2004 | Tallarida et al. | |
| 2004/0106928 A1* | 6/2004 | Ek | 606/96 |
| 2004/0148030 A1 | 7/2004 | Ek | |
| 2004/0158255 A1 | 8/2004 | Justin et al. | |
| 2004/0199166 A1* | 10/2004 | Schmieding et al. | 606/79 |
| 2004/0204722 A1 | 10/2004 | Sikora et al. | |
| 2004/0230315 A1 | 11/2004 | Ek | |
| 2005/0033363 A1 | 2/2005 | Bojarski et al. | |
| 2005/0119664 A1 | 6/2005 | Carignan et al. | |
| 2005/0125031 A1 | 6/2005 | Pipenhagen et al. | |
| 2005/0154398 A1 | 7/2005 | Miniaci et al. | |
| 2005/0154998 A1 | 7/2005 | Mathieson | |
| 2005/0190002 A1 | 9/2005 | Takinami et al. | |
| 2005/0229726 A1 | 10/2005 | Schubert et al. | |

(56) References Cited

U.S. PATENT DOCUMENTS

| | | |
|---|---|---|
| 2005/0251159 A1 | 11/2005 | Ewers et al. |
| 2006/0019002 A1 | 1/2006 | Xue |
| 2006/0020343 A1 | 1/2006 | Ek |
| 2006/0069394 A1 | 3/2006 | Weiler et al. |
| 2006/0085006 A1 | 4/2006 | Ek et al. |
| 2006/0190002 A1 | 8/2006 | Tallarida et al. |
| 2006/0195112 A1 | 8/2006 | Ek |
| 2006/0212055 A1 | 9/2006 | Karabey et al. |
| 2006/0229726 A1 | 10/2006 | Ek |
| 2007/0005143 A1 | 1/2007 | Ek et al. |
| 2007/0010857 A1 | 1/2007 | Sugimoto et al. |
| 2007/0021838 A1 | 1/2007 | Dugas et al. |
| 2007/0032800 A1 | 2/2007 | Ortiz et al. |
| 2007/0088442 A1 | 4/2007 | Cima et al. |
| 2007/0108136 A1 | 5/2007 | Gold |
| 2007/0118136 A1 | 5/2007 | Ek |
| 2007/0123921 A1 | 5/2007 | Ek |
| 2007/0179608 A1 | 8/2007 | Ek et al. |
| 2007/0233128 A1 | 10/2007 | Schmieding et al. |
| 2007/0250067 A1 | 10/2007 | Schmieding et al. |
| 2008/0033443 A1 | 2/2008 | Sikora et al. |
| 2008/0058949 A1 | 3/2008 | Dees et al. |
| 2008/0082127 A1 | 4/2008 | Stone et al. |
| 2008/0082128 A1 | 4/2008 | Stone |
| 2008/0172125 A1 | 7/2008 | Ek |
| 2008/0183174 A1 | 7/2008 | Sikora et al. |
| 2008/0195113 A1 | 8/2008 | Sikora |
| 2008/0275512 A1 | 11/2008 | Albertorio et al. |
| 2009/0018655 A1 | 1/2009 | Brunelle et al. |
| 2009/0082650 A1 | 3/2009 | Wilson et al. |
| 2009/0149858 A1 | 6/2009 | Fanelli et al. |
| 2009/0192516 A1 | 7/2009 | Tallarida et al. |
| 2009/0216285 A1 | 8/2009 | Ek et al. |
| 2009/0222012 A1 | 9/2009 | Karnes et al. |
| 2009/0240335 A1 | 9/2009 | Arcenio et al. |
| 2010/0070045 A1 | 3/2010 | Ek |
| 2010/0070048 A1 | 3/2010 | Tallarida et al. |
| 2010/0185294 A1 | 7/2010 | Ek |
| 2010/0191245 A1 | 7/2010 | Ek et al. |
| 2010/0191340 A1 | 7/2010 | Dreyfuss |
| 2010/0204701 A1 | 8/2010 | Tallarida et al. |
| 2010/0268238 A1 | 10/2010 | Sikora et al. |
| 2010/0268239 A1 | 10/2010 | Sikora et al. |
| 2010/0280465 A1 | 11/2010 | Tallarida et al. |
| 2010/0312342 A1 | 12/2010 | Ek |
| 2011/0054419 A1 | 3/2011 | Eliasen |
| 2011/0071641 A1 | 3/2011 | Ek et al. |
| 2011/0137288 A1 | 6/2011 | Tallarida et al. |
| 2011/0152869 A1 | 6/2011 | Ek et al. |
| 2011/0152870 A1 | 6/2011 | Miniaci et al. |
| 2011/0196434 A1 | 8/2011 | Ek et al. |
| 2011/0213375 A1 | 9/2011 | Sikora et al. |
| 2011/0238074 A1 | 9/2011 | Ek |
| 2011/0264141 A1 | 10/2011 | Denham et al. |
| 2012/0004663 A1 | 1/2012 | Tallarida et al. |
| 2012/0191187 A1 | 7/2012 | Tallarida et al. |
| 2012/0330316 A1 | 12/2012 | Berelsman et al. |
| 2012/0330317 A1 | 12/2012 | Berelsman et al. |

FOREIGN PATENT DOCUMENTS

| | | |
|---|---|---|
| EP | 0661023 A2 | 7/1995 |
| EP | 1013231 A2 | 6/2000 |
| EP | 1013232 A2 | 6/2000 |
| EP | 1374782 A2 | 1/2004 |
| EP | 2723253 A1 | 4/2014 |
| FR | 2737970 A1 | 2/1997 |
| FR | 2808182 A1 | 11/2001 |
| WO | WO-9533414 A1 | 12/1995 |
| WO | WO-9956674 A1 | 11/1999 |
| WO | WO-0182804 A1 | 11/2001 |
| WO | WO-0182838 A2 | 11/2001 |
| WO | WO-03051210 A2 | 6/2003 |
| WO | WO-2006056751 A1 | 6/2006 |
| WO | WO-2007092841 A2 | 8/2007 |
| WO | WO-2010124164 A1 | 10/2010 |
| WO | WO-2013003347 A1 | 1/2013 |

OTHER PUBLICATIONS

International Preliminary Report on Patentability and Written Opinion mailed Jan. 16, 2014 for PCT/US2012/044198 claiming benefit of U.S. Appl. No. 13/169,075, filed Jun. 27, 2011.

International Search Report and Written Opinion mailed Nov. 20, 2012 for PCT/US2012/044198 claiming benefit of U.S. Appl. No. 13/169,075, filed Jun. 27, 2011.

Invitation to Pay Additional Fees mailed Sep. 27, 2012 for PCT/US2012/044198 claiming benefit of U.S. Appl. No. 13/169,075, filed Jun. 27, 2011.

RetroConstruction-MinimallyInvasiveOptions__Arthrex-brochure-11pp__2009.

* cited by examiner

APPARATUS FOR REPAIRING BONE DEFECTS

CROSS REFERENCE TO RELATED APPLICATIONS

This application is a divisional of U.S. patent application Ser. No. 13/169,075 filed on Jun. 27, 2011.

This application is also related to U.S. patent application Ser. No. 13/169,074 filed on Jun. 27, 2011. The disclosures of the above applications are incorporated by reference herein.

FIELD

The present disclosure relates generally to an apparatus for repairing soft tissue and/or bone defects, and more particularly to an apparatus for repairing cartilage and/or bone defects in a knee joint.

BACKGROUND

This section provides background information related to the present disclosure which is not necessarily prior art.

Articular cartilage enables bones to move smoothly relative to one another, as is known in the art. Damage to articular cartilage, such as in a knee joint, can be caused by injury, such as tearing, by excessive wear, or by a lifetime of use. Such damage to the articular cartilage can also cause damage to the underlying bone. The damaged articular cartilage can lead to, in certain circumstances, pain and reduced mobility. Various surgical procedures have been developed to repair damaged articular cartilage, such as microfracture, OATS, mosaicplasty or a unicondylar or partial knee replacement.

While these surgical procedures are effective for their intended purpose, there remains a need for improvement in the relevant art for treating focal defects in articular cartilage in a minimally invasive manner.

SUMMARY

This section provides a general summary of the disclosure, and is not a comprehensive disclosure of its full scope or all of its features.

In one form, a system for repairing a soft tissue or bone defect is provided according to the teachings of the present disclosure. The system can include a plurality of sizing guides, a plurality of perimeter cutting devices, a cutting member, a cutting member guide, and a plurality of implants. Each of the plurality of sizing guides can include a base with a different perimeter size and a plurality of cannulated guide shafts extending from one side of the base opposite a bone engaging side of the base. The base can define a plurality of apertures aligned with the plurality of cannulated guide shafts. The plurality of apertures and cannulated guide shafts can be adapted to receive a plurality of guide wires adapted to be removably fixed to a first bone associated with the defect. The plurality of perimeter cutting devices can each have a base with a perimeter size corresponding to the different perimeter size of the base of each of the plurality of sizing guides. Each base of the plurality of perimeter cutting devices can have a cutting edge on a perimeter thereof and can define a plurality of apertures corresponding in location to the plurality of apertures in each base of the plurality of sizing guides such that the plurality of perimeter cutting devices are adapted to be slidably received on and guided by the plurality of guide wires. The cutting member can be adapted to be separately slidably received over at least one of the plurality of guide wires to form a pocket in the first bone relative to the defect. The cutting member guide can be configured to be received over the plurality of guide wires and can have at least one aperture configured to receive a portion of the cutting member therein. The plurality of implants can have a perimeter size and shape corresponding to each base of the perimeter cutting devices, where the plurality of implants can be adapted to be implanted into the pocket formed in the first bone. The plurality of apertures in the bases of the plurality of sizing guides and perimeter cutting devices can be spaced apart by a predetermined distance, where the predetermined distance is the same in each of the plurality of sizing guides and perimeter cutting devices.

In another form, a system for repairing a soft tissue or bone defect is provided according to the teachings of the present disclosure. The system can include a first guide and a first cutting member. The first guide can be adapted to be positioned relative to a distal end of a first bone. The first guide can include a base having a bone engaging side and a cannulated guide shaft extending from an opposite side of the base. The first cutting member can be configured to be received in the cannulated guide shaft and can be adapted to be advanced toward to the first bone to form a bore through the first bone. The first cutting member can include first and second ends and an intermediate portion extending between the first and second ends. The first end can include a first cutting portion forming a terminal end thereof and a cutting device engaging portion adjacent the first cutting portion. The second end can include a second cutting portion extending from a terminal end thereof toward the intermediate portion and a driver engaging portion between the second cutting portion and the intermediate portion.

In yet another form, a system for repairing a soft tissue or bone defect is provided according to the teachings of the present disclosure. The system can include a sizing guide, a perimeter cutting member, a first cutting member, a first cutting member stop guide, a second cutting member stop guide, a drill member, a drill member guide, a cutting device, a drive collar, and a cannulated stop member. The sizing guide can have a base and a plurality of cannulated shafts extending from one side of the base opposite a bone engaging side of the base. The base can define a plurality of apertures aligned with the plurality of cannulated shafts. The cannulated shafts can be spaced apart a predetermined distance from each other and can be adapted to receive a plurality of guide wires configured to be located by the plurality of cannulated shafts and adapted to be fixed to a bone associated with the defect. The perimeter cutting member can have a base with a perimeter sized to correspond with a perimeter of the base of the sizing guide. The perimeter cutting member can include a cutting edge adapted to cut a perimeter outline in soft tissue proximate the defect, and can define a plurality of apertures corresponding to the plurality of apertures in the sizing guide such that the perimeter cutting member is adapted to be positioned over the plurality of guide wires. The first cutting member can have a longitudinal throughbore and a cutting portion on a bone engaging side extending to a stop collar. The first cutting member stop guide can define a first pair of outer apertures configured to receive the cutting portion of the first cutting member therein, where the first pair of outer apertures can be configured to be received over outer guide wires of the plurality of guide wires. The first pair of outer apertures can be sized and shaped to separately receive and guide the cutting portion of the first cutting member relative to the respective outer guide wires. The second cutting member stop guide can define a central aperture configured to be received over the central guide wire positioned between the outer guide wires and a second pair of outer apertures. The central aperture can be sized and shaped to receive and guide the first cutting member relative to the central guide wire and the second cutting member stop guide. The drill member can have a first end with a first cutting portion and a cutting device attachment portion adjacent thereto, and a second opposite end having a second cutting portion and a driver engaging portion adjacent thereto. The drill member guide can have a base and a cannulated guide shaft extending at an acute angle therefrom, where the drill member cannulated guide shaft can be configured to receive the drill member therethrough. The cutting device can be configured to be coupled to the attachment portion of the first end of the drill member extending from one side of the drill member guide shaft. The drive collar can be configured to be coupled to the second end of the drill member so as to cover the second cutting portion and can be adapted to facilitate rotatably driving the drill member relative to the drill member guide. The cannulated stop member can be configured to be positioned over the second end of the drill member and limit an amount of travel of the drill member relative to the drill member guide.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

FIG. 1A is a perspective view of the sizing guide of FIG. 1 in accordance with the teachings of the present disclosure;

DETAILED DESCRIPTION

Figure 1:
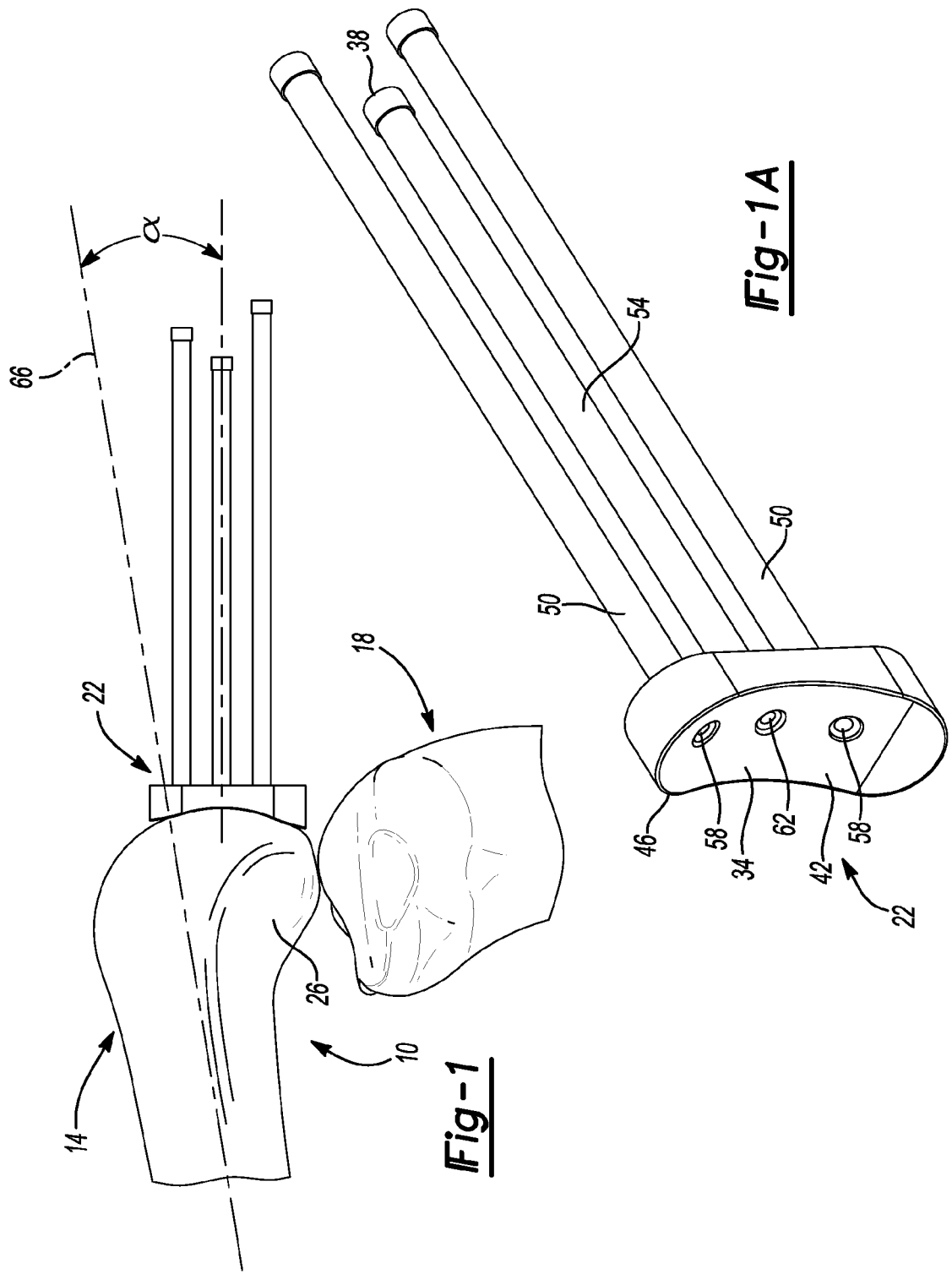
FIG. 1 is a perspective view depicting an exemplary surgical procedure including positioning a sizing guide relative to a cartilage defect in accordance with the teachings of the present disclosure.

The following description is merely exemplary in nature and is not intended to limit the present disclosure, its application, or uses. It should be understood that throughout the drawings, corresponding reference numerals indicate like or corresponding parts and features. Although the following description is related generally to methods and systems for repairing a cartilage defect in a knee joint, it should be appreciated that the methods and systems discussed herein can be applicable to other bones and/or joints of the anatomy.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Turning now to FIGS. 1-16A of the drawings, various methods and systems are disclosed in accordance with the present teachings for repairing a cartilage defect in a knee joint 10. As will be discussed in greater detail below, pockets in a femur 14 and tibia 18 can be formed for receiving respective implants, with the tibial pocket being formed via access through a bore in the femur 14 in accordance with an exemplary aspect of the present teachings.

Figure 16:
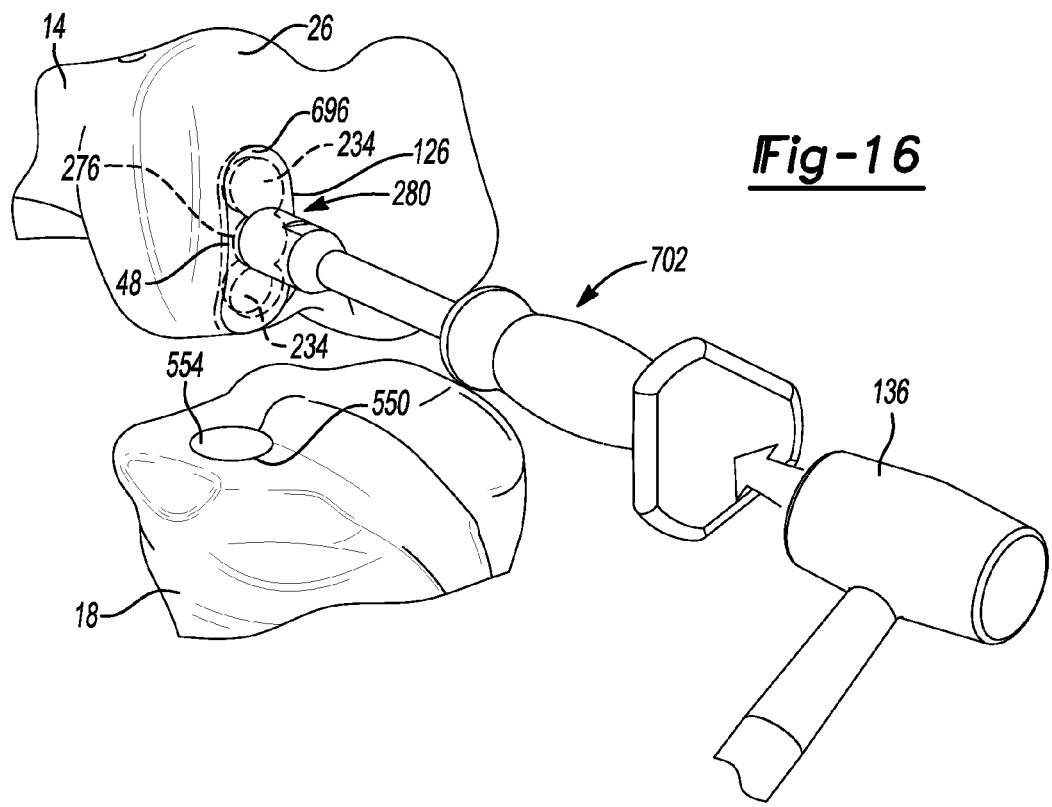
FIG. 16 is a perspective view of the exemplary procedure depicting positioning a femoral implant relative to the femoral pocket in accordance with the teachings of the present disclosure.
Figure 16A:
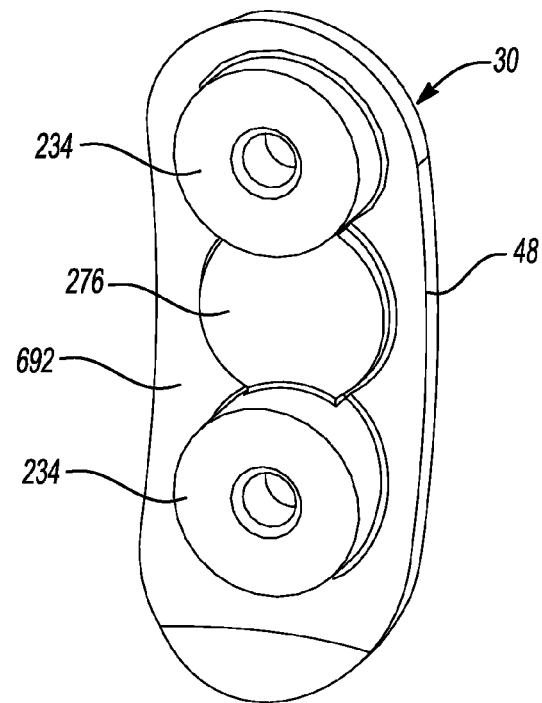
FIG. 16A is a perspective view of the femoral implant of FIG. 16 in accordance with the teachings of the present disclosure.

With particular reference to FIGS. 1 and 1A, knee joint 10 is shown in flexion and an exemplary sizing guide 22 is shown positioned relative to a defect or lesion in the articular cartilage on one of the femoral condyles 26. As will be discussed in greater detail below, sizing guide 22 can be used to determine an appropriate size and location for a femoral implant 30 (FIG. 16A). Sizing guide 22 can include a first or bone engaging end or surface 34 and an opposite second end 38. The bone engaging surface 34 can include an arcuate shape to match the contour of the distal end of the femoral condyles 26. The bone engaging end 34 can include a base 42 having an outer perimeter 46 that corresponds in size and shape to an outer perimeter 48 of the femoral implant 30. In this regard, sizing guide 22 can be provided with base 42 having a variety of different sizes that correspond to a variety of correspondingly sized femoral implants so as to best match the size of the patient's cartilage defect.

A pair of cannulated outer shafts 50 and an inner or central cannulated shaft 54 can extend from the base 42 and can define the opposite end 38. Shafts 50 and 54 can align with corresponding through bores 58 and 62, respectively, formed in base 42, as shown in FIG. 1A. In one exemplary configuration, shafts 50 and 54 can include different axial lengths so as to have staggered ends to facilitate ease of use, as shown for example in FIGS. 1 and 1A. The through bores 58 and 62 can be positioned at a predetermined distance relative to each other and remain in the same position regardless of the different sizes provided for base 42.

Once an appropriate sizing guide 22 has been selected that has a base 42 corresponding to the size of the defect or that best matches with the size of the defect, the base 42 can be positioned over the defect such that the inner shaft 54 is aligned at an angle α of about 30 to 40 degrees below or posterior to a longitudinal axis 66 of femur 14, as shown in FIG. 1.

Figure 2:
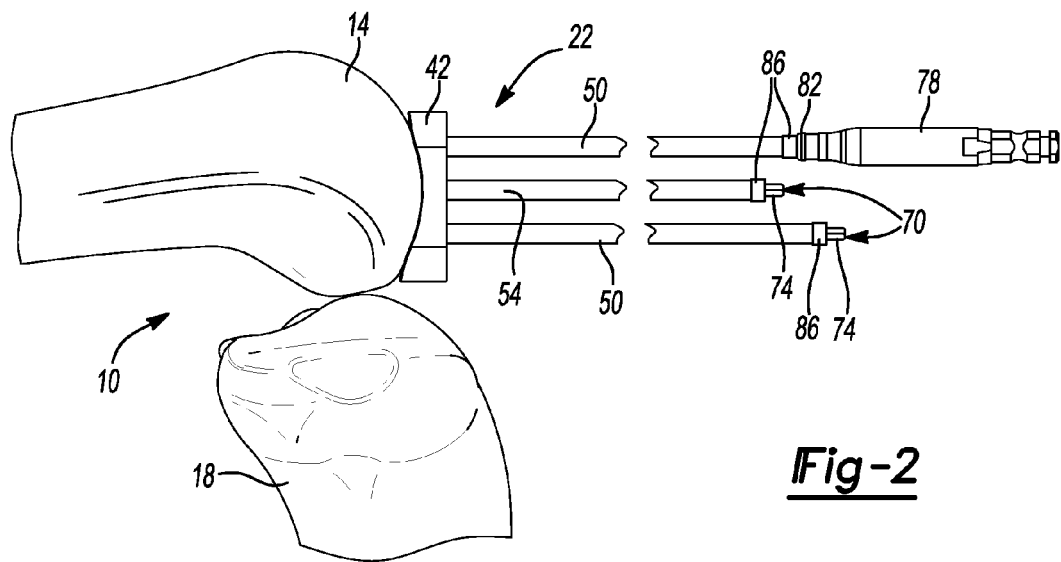
FIG. 2 is a perspective view of the exemplary procedure depicting positioning guide pins relative to the sizing guide and the femur in accordance with the teachings of the present disclosure.

Referring to FIG. 2, with the sizing guide 22 positioned as discussed above, a guide pin 70, such as a K-wire with a threaded distal tip, can be inserted into each of the cannulated tubes to provide three distinct separate axes for guidance. The guide pins 70 can include a hex or other shaped proximal end 74 configured to receive a driver 78. Driver 78 can be used to drive the threaded distal tips of guide pins 70 into femur 14. In this regard, the guide pins 70 can include a length correlating to a length of outer shafts 50 and inner shaft 54 such that the guide pins 70 can be driven into femur 14 until a distal end 82 of driver 78 engages ends 86 of shafts 50 and 54. For discussion purposes, the guide pin 70 corresponding to the inner shaft will hereinafter be referred to as the inner guide pin 70 and the guide pins 70 corresponding to the outer shafts 50 will be referred to as the outer guide pins 70.

As will be discussed in greater detail below, the implanted guide pins 70 can serve as a guidance system for other instruments and/or procedures to be performed in connection with repairing the cartilage defect in accordance with the teachings of the present disclosure. Once the guide pins 70 have been implanted as discussed above, the sizing guide 22 can be removed by sliding the guide 22 away from femur 14 about guide pins 70. In one exemplary configuration, the sizing guide 22 can be reusable and formed of a biocompatible material, such as stainless steel, titanium, or the like, consistent with such purpose.

Figure 3:
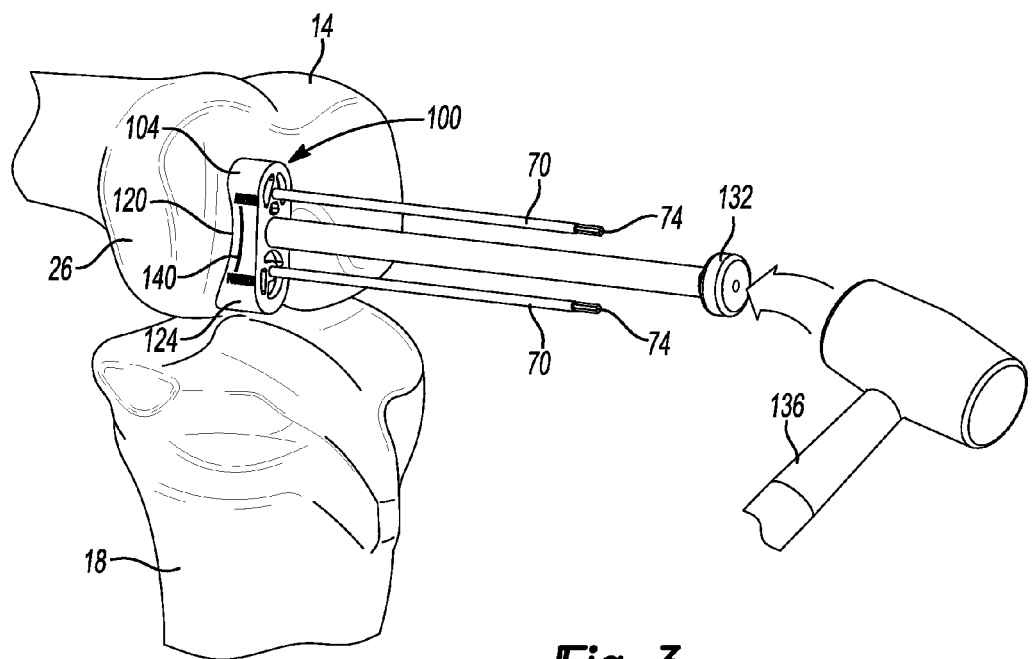
FIG. 3 is a perspective view of the exemplary procedure depicting positioning a cartilage cutter relative to the guide pins and femur in accordance with the teachings of the present disclosure.
Figure 3A:
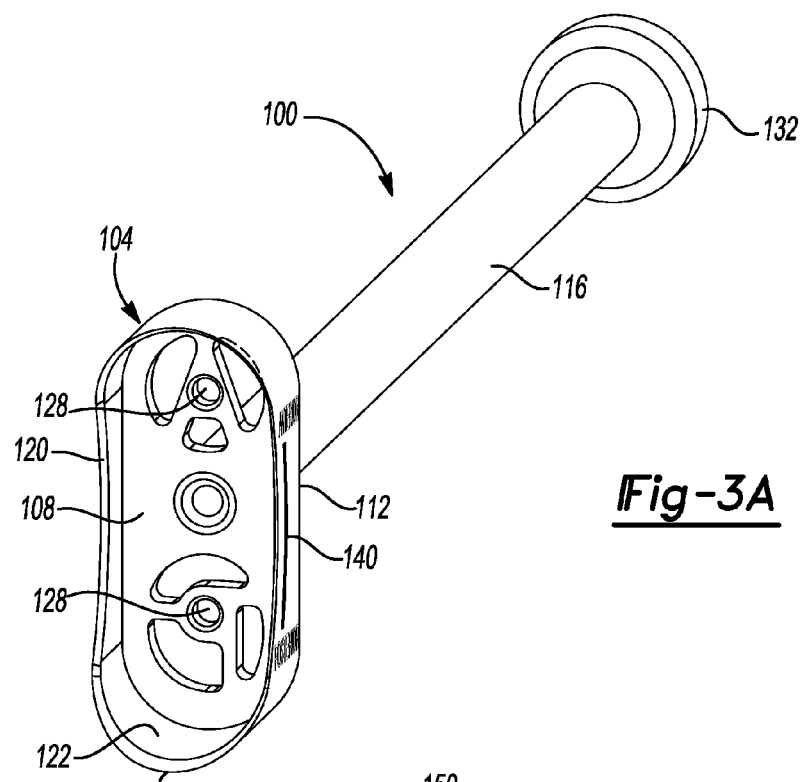
FIG. 3A is a perspective view of the cartilage cutter of FIG. 3 in accordance with the teachings of the present disclosure.

With particular reference to FIGS. 3 and 3A, an appropriately sized cartilage cutter 100 can be selected and positioned relative to the cartilage defect about guide pins 70. Cartilage cutter 100 can include a base 104 having a bone engaging end 108 and an opposite end 112 from which a cannulated impact shaft 116 extends. The cartilage cutter 100 can be provided in various sizes where an outer perimeter 120 of the base 104 varies in size and/or shape to correspond with the various sizes of femoral implant 30 and thus base 42 of sizing guide 22. The bone engaging end 108 of base 104 can include an outer rim 122 having a sharpened cutting edge 124 extending longitudinally from end 112 and can be used to cut an outline 126 (FIG. 9) in the cartilage around the defect that corresponds to the outer perimeter 120 of cartilage cutter 100.

End 112 of base 104 can include a pair of apertures 128 positioned on opposite sides of shaft 116 so as to correspond with the spacing of outer guide pins 70 implanted in femur 14. As briefly discussed above and shown in FIG. 3, cartilage cutter 100 can be slidably received on guide pins 70 via apertures 128 and cannulated shaft 116 so as to position outer cutting edge 124 of base 104 against the cartilage of femur 14. An impact end 132 of shaft 116 can be impacted with an impact member 136 to cut the outline 126 in the cartilage corresponding to the outer perimeter 48 of the selected femoral implant 30 (FIG. 16A). In this regard, it should be appreciated that the shaft 116 and impact end 132 include an axial length longer than the inner guide pin 70, as shown for example in FIG. 3. Base 104 of cartilage cutter 100 can also include indicia 140 providing a visual indication of a desired or maximum depth for driving cartilage cutter 100 relative to the femur. Once the cartilage has been cut with cartilage cutter 100, the cartilage cutter 100 can be removed in a similar manner as sizing guide 22 discussed above.

As will be discussed in greater detail below, by cutting the outline 126 in the cartilage, any tearing of cartilage outside the cut perimeter as a result of subsequent drilling in femur 14 can be substantially mitigated or eliminated. In this regard, in one exemplary configuration, only the outline 126 can be cut in the cartilage with cartilage cutter 100 such that cartilage is not removed by the cutting technique discussed above. However, it should be appreciated that cartilage within the perimeter outline cut into the cartilage could be removed in connection with cutting the perimeter outline into the femoral cartilage.

In one exemplary configuration, cartilage cutter 100 can be formed as a two-piece component where shaft 116 is removably engaged to base 104 via a threaded connection or the like. In this configuration, shaft 116 can be reusable and base 104 can be disposable.

Figure 4:
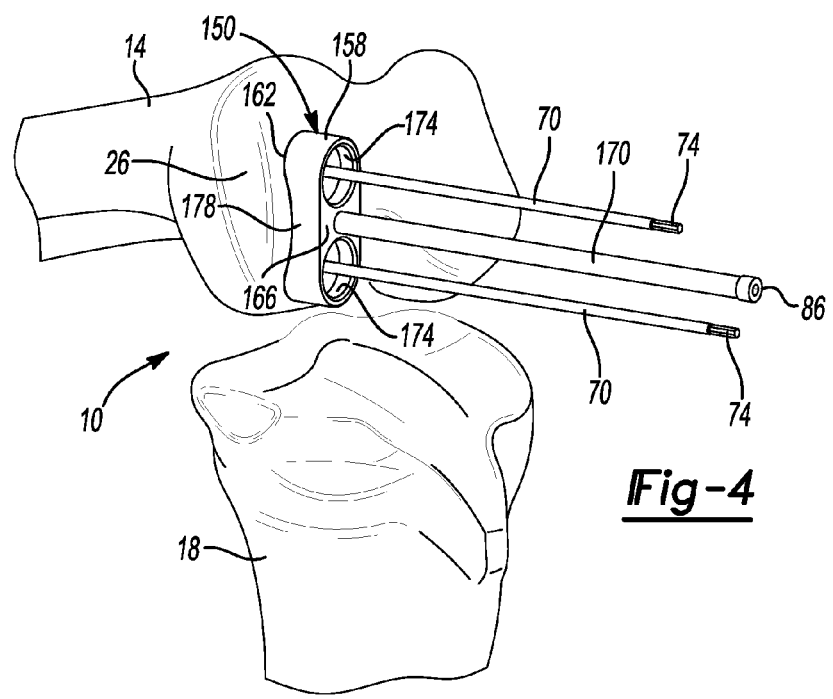
FIG. 4 is a perspective view of the exemplary procedure depicting positioning an outer drill stop relative to the guide pins and femur in accordance with the teachings of the present disclosure.
Figure 5:
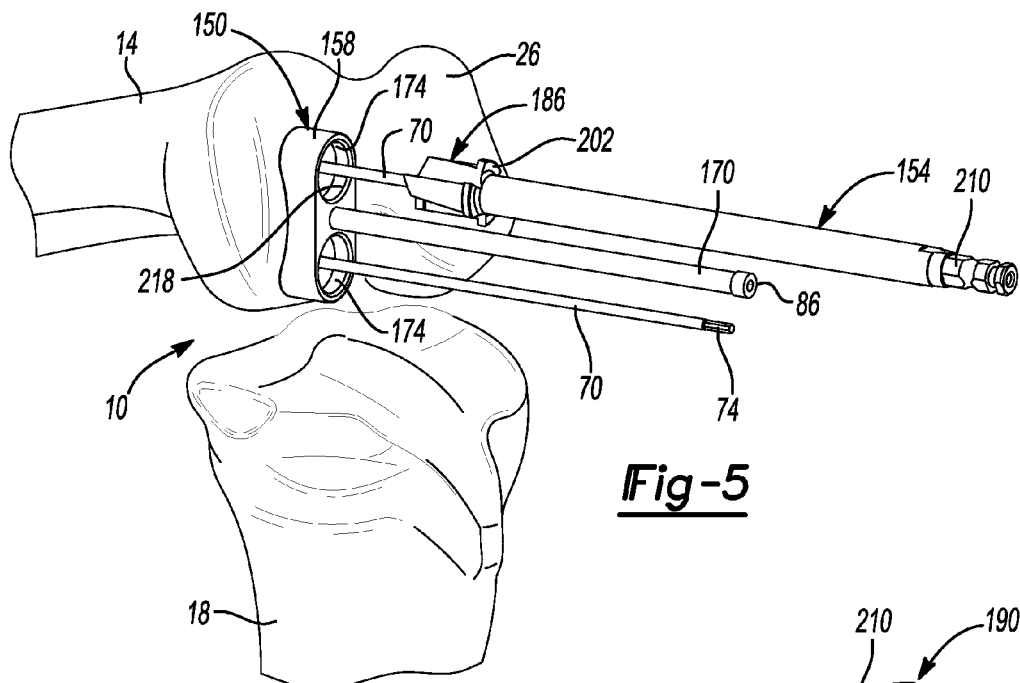
FIG. 5 is a perspective view of the exemplary procedure depicting a drill bit guided by one of the guide pins and the outer drill stop in accordance with the teachings of the present disclosure.
Figure 5A:
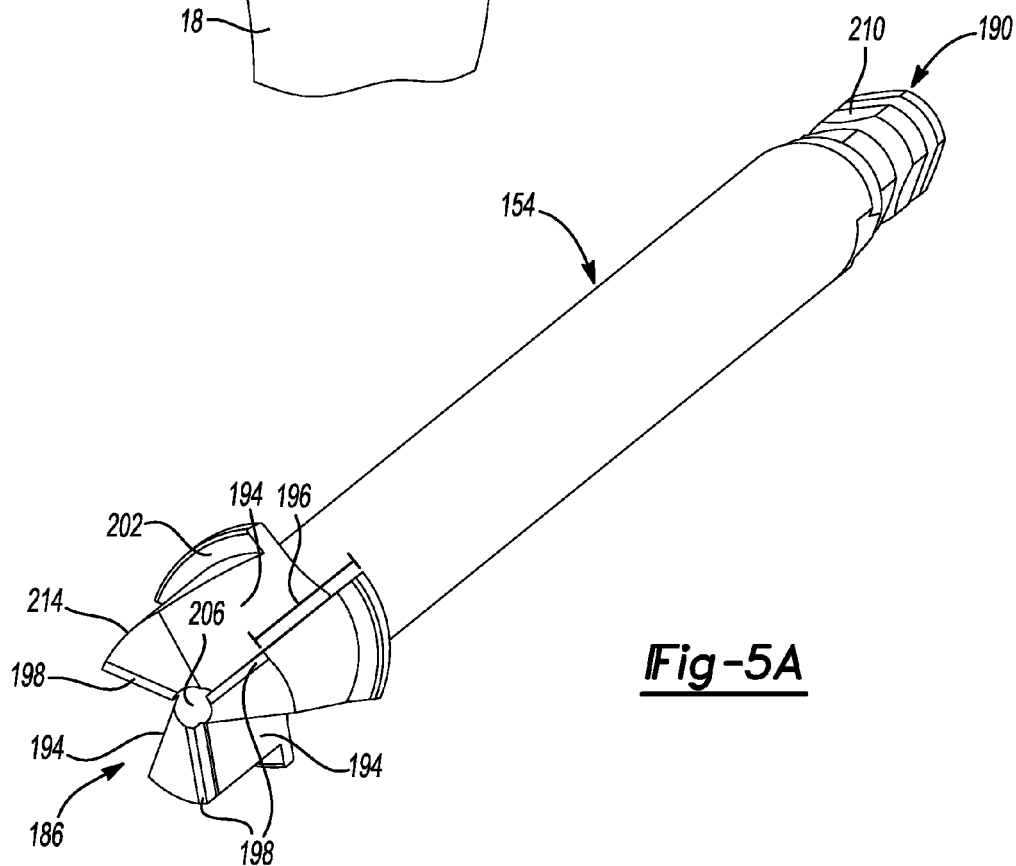
FIG. 5A is a perspective view of the drill bit of FIG. 5 in accordance with the teachings of the present disclosure.

With continuing reference to FIGS. 4-5A, an outer drill stop 150 can be positioned relative to femur 14 about guide pins 70, as shown in FIG. 4. As will be discussed below, outer drill stop 150 can serve to both guide a drill bit 154 relative to the cartilage defect as well as limit a drilling depth relative to femur 14. The outer drill stop 150 can include a base 158 having a bone engaging end 162 and an opposite end 166 from which a cannulated shaft 170 extends. Base 158 can include two apertures 174 having an inner diameter corresponding to an outer diameter of a portion of drill bit 154, as will be discussed below. Outer drill stop 150 can be positioned about guide pins 70 such that the outer guide pins 70 are received through apertures 174 and the inner guide pin 70 is received in cannulated shaft 170. In this regard, as can be seen in FIG. 4, cannulated shaft 170 in cooperation with inner guide pin 70 serves to initially guide outer drill stop 150 relative to femur 14. In one exemplary configuration, base 158 can include an outer perimeter 178 sized and shaped to also correspond with the outer perimeters of the selected cartilage cutter 100 and femoral implant 30.

Drill bit 154 can include a first or bone engaging end 186 and an opposite second or driver engaging end 190, as shown for example in FIG. 5A. The bone engaging end 186 can include a plurality of flutes 194 corresponding to a plurality of cutting edges 198, as also shown in FIG. 5A. In the exemplary configuration shown, drill bit 154 includes three flutes 194 between the corresponding three cutting edges 198. The flutes 194 can extend from the bone engaging end 186 for a length 196 to a stop collar 202. In one exemplary configuration, the flutes 194 can extend through the stop collar 202 so as to provide a path for bone material to exit the drill bit 154 during use. Drill bit 154 can also include throughbore 206 sized and shaped to cooperate with the outer guide pins 70 and a driver engagement portion 210 at the driver engaging end 186 configured to cooperate with a drill bit driving member (not shown).

In use, drill bit 154 can be separately positioned about each of the outer guide pins 70 such that the pins are received in the throughbore 206 of drill bit 154. An outer diameter 214 of the bone engaging end 186 can be sized to cooperate with an inner diameter 218 of outer drill stop apertures 174, as shown in FIG. 5 with reference to FIG. 4. In this regard, as the drill bit 154 is advanced along each of the outer guide pins 70 into respective apertures 174, the bone engaging end 186 can cooperate with the respective aperture 174 and outer guide pin 70 to self-center that aperture 174 about the associated outer guide pin 70. Drill bit 154 can be advanced relative to femur 14 until stop collar 202 engages base 158, thereby limiting a depth of outer bores or pockets 226 (FIG. 9) drilled in femur 14. As will be discussed in greater detail below, the inner diameter 230 of outer bores 226 can correspond to an outer diameter of corresponding outer projections 234 (FIG. 16A) on femoral implant 30.

Figure 6:
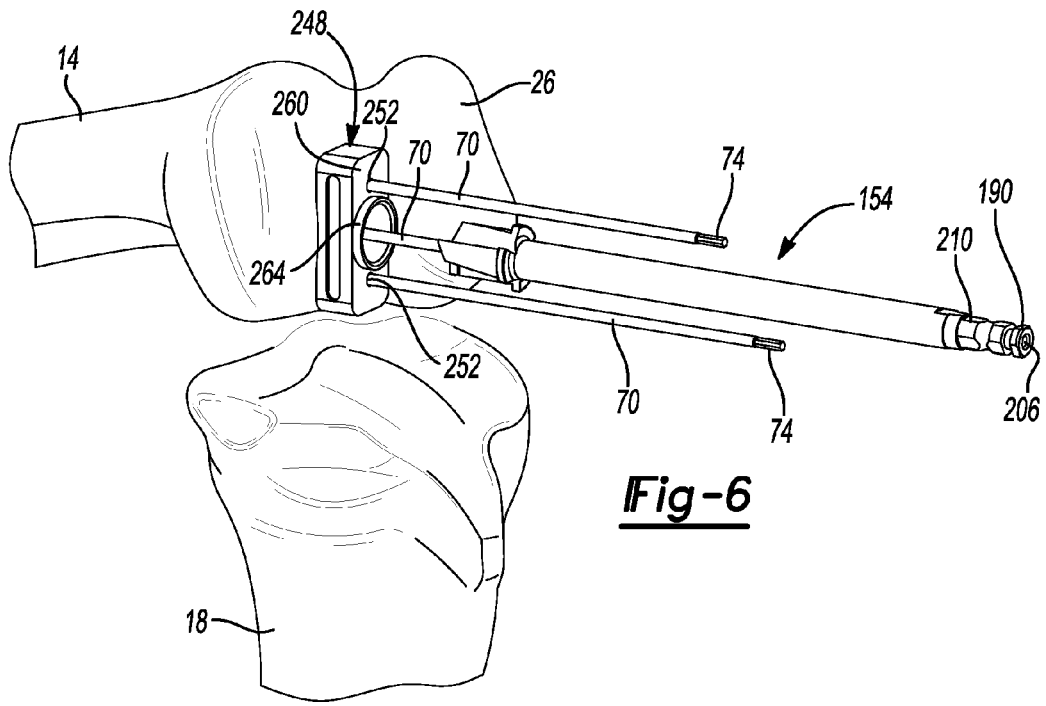
FIG. 6 is a perspective view of the exemplary procedure depicting the drill bit guided by one of the guide pins and an inner drill stop in accordance with the teachings of the present disclosure.
Figure 6A:
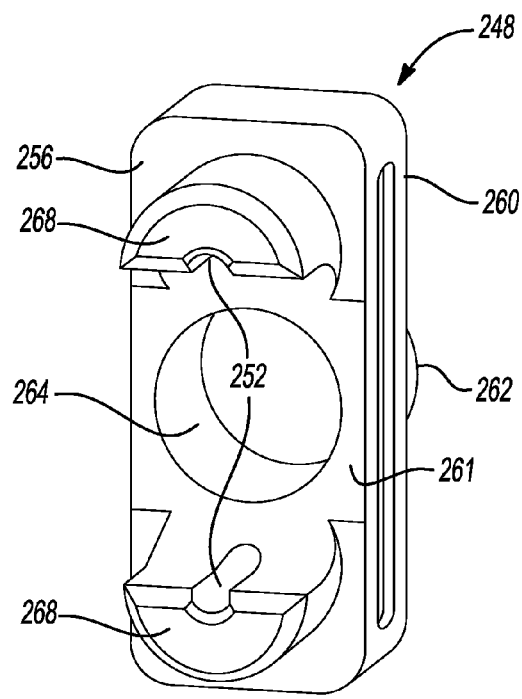
FIG. 6A is a perspective view of the inner drill stop of FIG. 6 in accordance with the teachings of the present disclosure.

With continuing reference to FIGS. 6 and 6a, the outer drill stop 150 can be removed after forming outer bores 226 while leaving guide pins 70 in place. An inner drill stop 248 can be positioned over outer guide pins 70 via corresponding apertures 252 and positioned relative to femur 14, as shown in FIG. 6. Inner drill stop 248 can include a first or bone engaging side 256, a second opposite side 260 and a central drill bit receiving aperture 264. Bone engaging side 256 can include a pair of projections 268 configured to be received in outer bores 226 (FIG. 9) to aid in locating and retaining inner drill stop 248 relative to bores 226 and femur 14, as shown in FIG. 6A.

Figure 9:
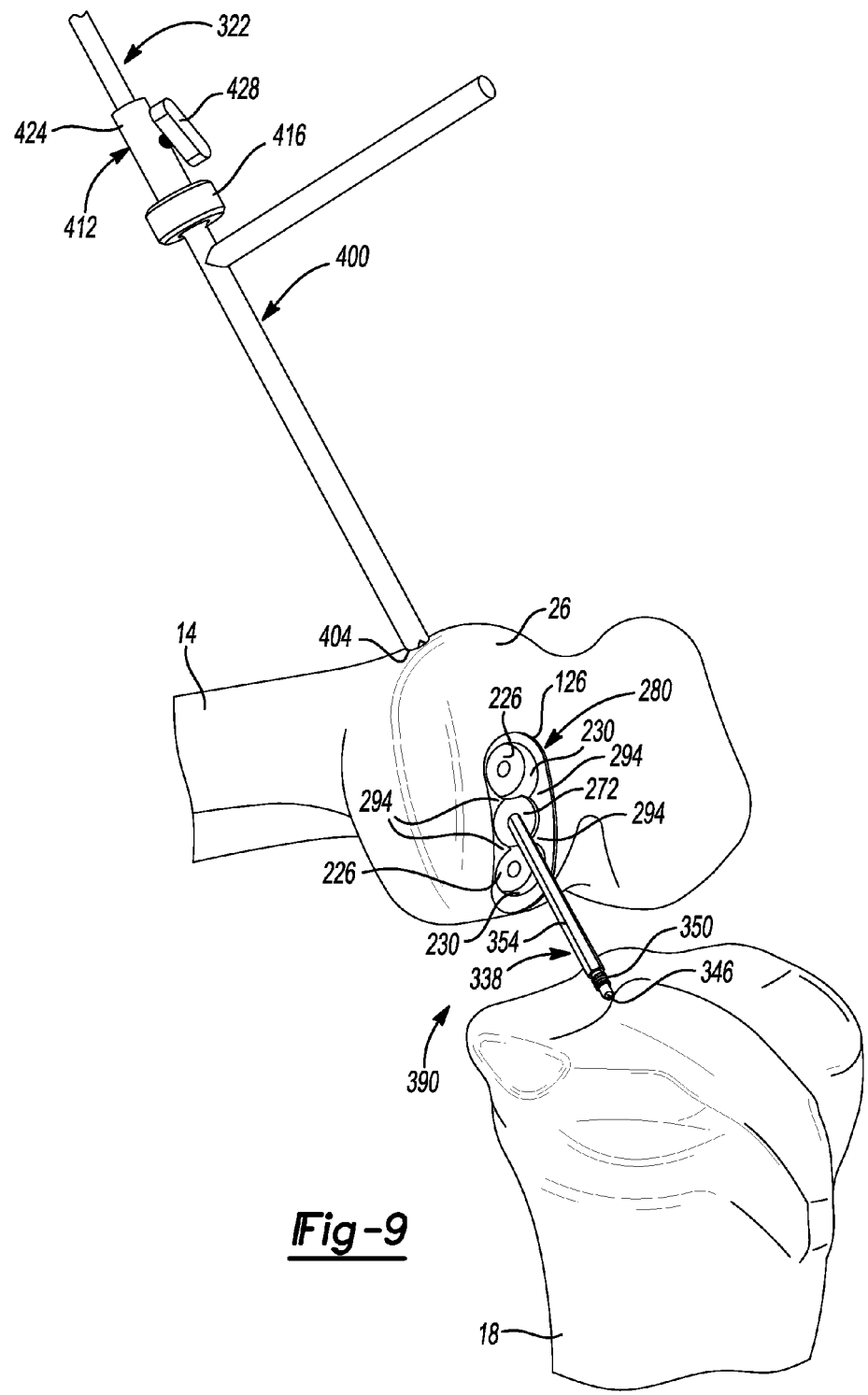
FIGS. 9-10 are perspective views of the exemplary procedure depicting preparing the drill bit for forming a pocket in the tibia in accordance with the teachings of the present disclosure.

In the exemplary configuration illustrated, projections 268 can be in the form of semicircles having a radius substantially corresponding to a radius of outer bores 226. With the inner drill stop 248 in place as shown in FIG. 6, drill bit 154 can be advanced over inner guide pin 70 and received in aperture 264 to drill an inner bore or pocket 272 (FIG. 9) in femur 14. In the exemplary configuration illustrated, inner bore 272 can include a depth less than a corresponding depth of outer bores 226, as shown in FIG. 9, corresponding to outer projections 234 and an inner projection 276 of femoral implant 30, as shown in FIG. 16A. In this regard, since drill bit 154 can be used for both the outer and inner bores 226, 272, a thickness of the inner drill stop between ends 261, 262 can be greater than a corresponding thickness of the base of outer drill stop 150. The outer and inner bores 226, 272 can hereinafter also be referred to as the femoral or reference pocket 280 configured to receive the femoral implant 30 (FIG. 9).

Figure 7:
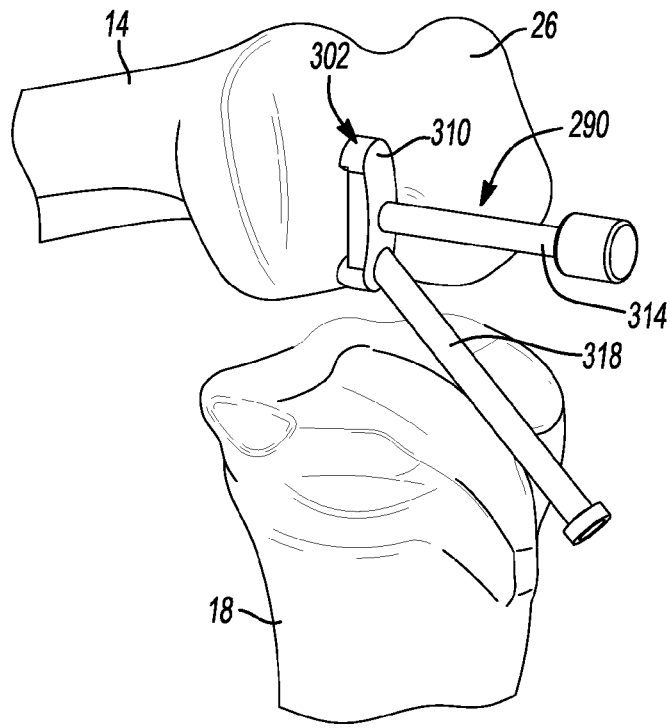
FIG. 7 is a perspective view of the exemplary procedure depicting a femoral drill guide positioned relative to the cartilage defect area of the femur in accordance with the teachings of the present disclosure.
Figure 8:
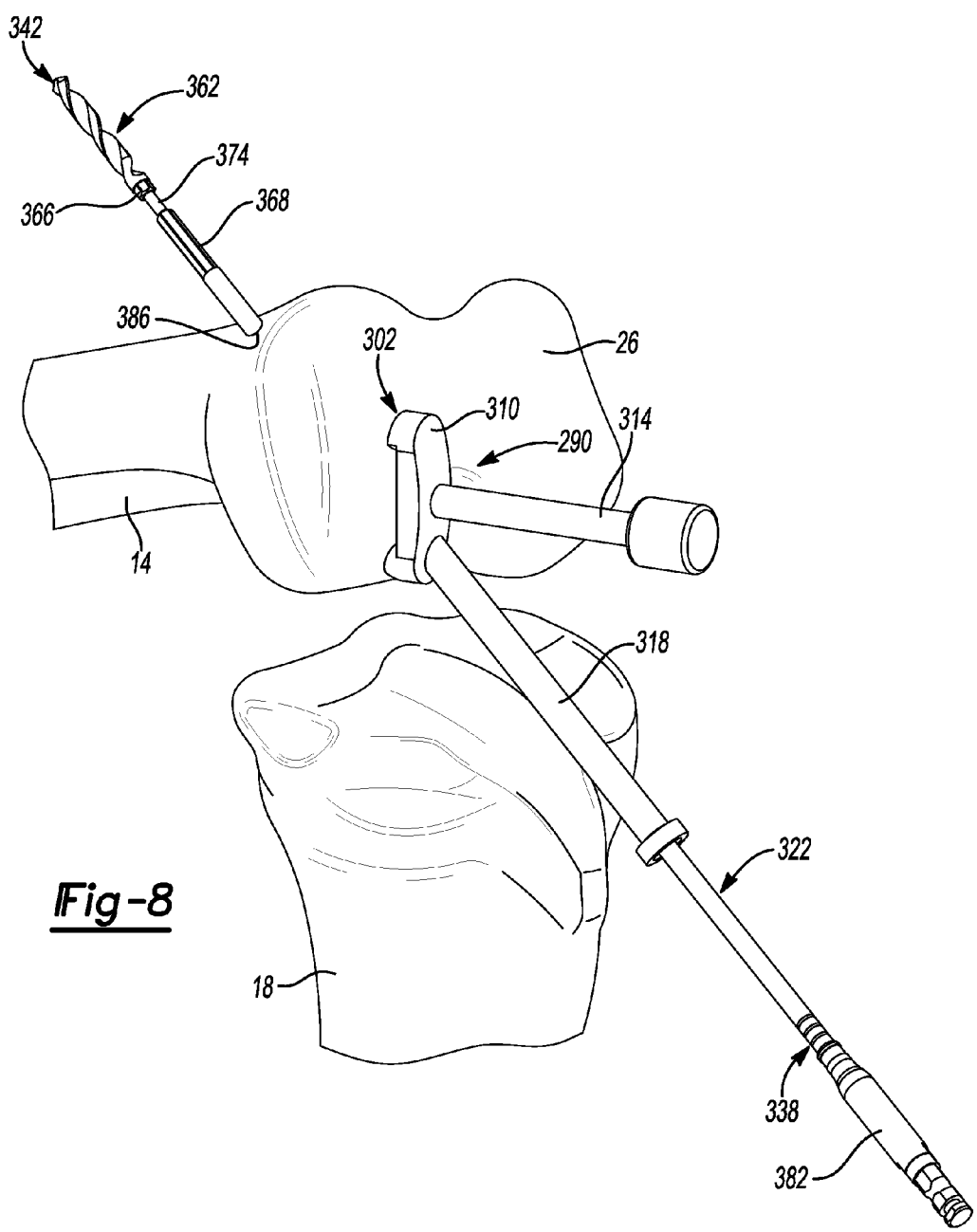
FIG. 8 is a perspective view of the exemplary procedure depicting forming a bore through the femur with a drill bit in accordance with the teachings of the present disclosure.

Referring additionally to FIGS. 7-8, the inner drill stop 248 can be removed along with the guide pins 70 after forming inner bore 272, and a drill guide 290 can be positioned relative to femur 14 using bores 226, 272 for locating reference and alignment. As will be discussed in greater detail below, drill guide 290 can be used to drill a bore in the femur 14, which will be used to prepare the tibia for receipt of a tibial implant. Before locating drill guide 290 relative to femur 14, any remaining cartilage between outline 126 and bores 226, 272 in areas 294 can be removed, as shown in FIG. 9. Once such cartilage is removed, drill guide 290 can be positioned relative to femur 14 using bores 226, 272, as will be discussed in greater detail below.

Figure 7A:
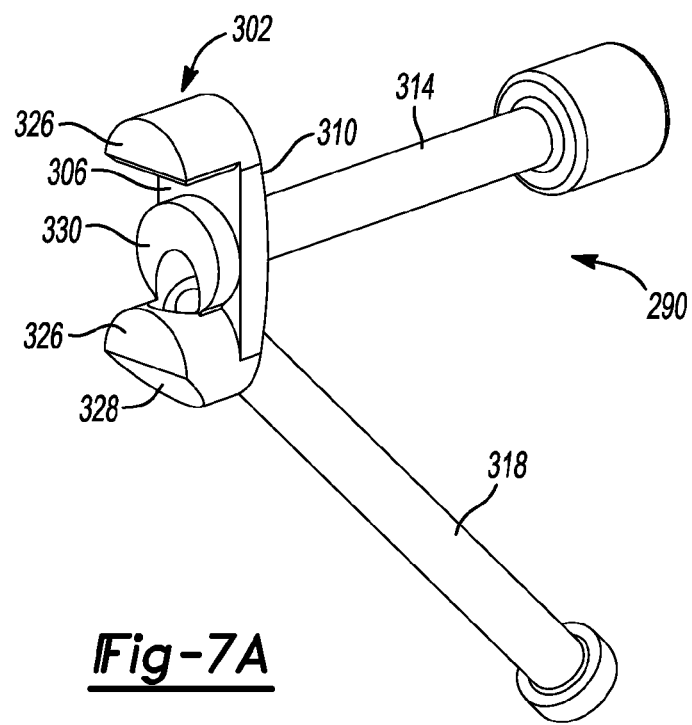
FIG. 7A is a perspective view of the femoral drill guide of FIG. 7 in accordance with the teachings of the present disclosure.

Drill guide 290 can include a base 302 having a first or bone engaging side 306 and a second opposite side 310. A handle 314 can extend from the second side of base 302 and perpendicular thereto, as shown in FIGS. 7 and 7A. A cannulated guide member 318 can also extend from base 302 at a 45 degree angle relative to both base 302 and handle 314. Guide member 318 can be configured to receive and guide a drill bit 322 (FIG. 8), as will be discussed below. The bone engaging side 306 can include outer and inner projections 326, 330 sized and shaped to correspond with and be received in bores 226, 272, as shown in FIG. 7A with reference to FIG. 7. The lower or posterior outer projection 326 can include an angled portion 328 configured to aid in removing drill guide 290 at an angle from bores 226, 272 about drill bit 322, as will be discussed below. Once drill guide 290 is positioned relative to bores 226, 272, drill bit 322 can be received in cannulated guide member 318 and advanced relative to femur 14 to drill a bore through femur 14, as shown in FIG. 8.

Figure 8A:
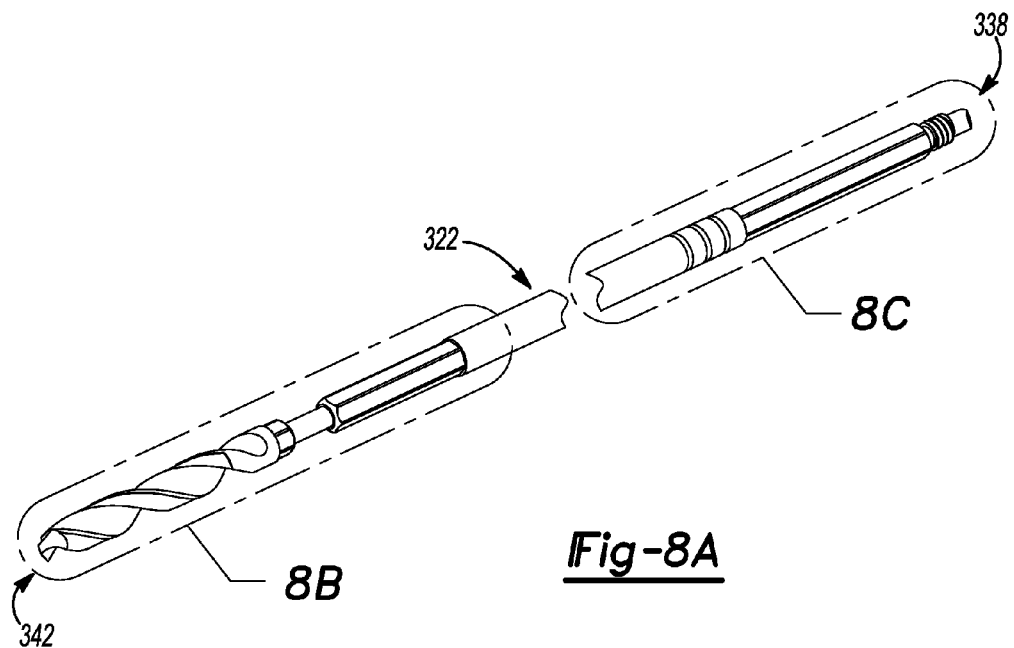
FIGS. 8A-8C depict views of the drill bit of FIG. 8 in accordance with the teachings of the present disclosure.

With additional reference to FIGS. 8A-8C, drill bit 322 will be discussed in greater detail. Drill bit 322 can include a first end 338 and a second end 342. First end 338 can include a pointed tip portion 346 configured to engage bone and assist in a cutting operation, followed by a threaded portion 350 and a first hexagon shaped portion in cross section 354, as shown for example in FIG. 8C. In the exemplary configuration illustrated, tip portion 346 can include a smaller diameter than threaded portion 350, which can include a smaller diameter than the first hexagon shaped portion 354, as shown in FIG. 8C. As will be discussed below in greater detail, first end 338 can receive both a quick-release driver to facilitate driving drill bit 322 through femur 14, and a cutter for forming a pocket in tibia 18.

Figure 8B:
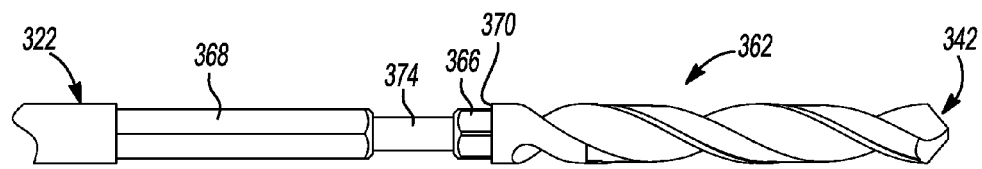
Figure 8C:
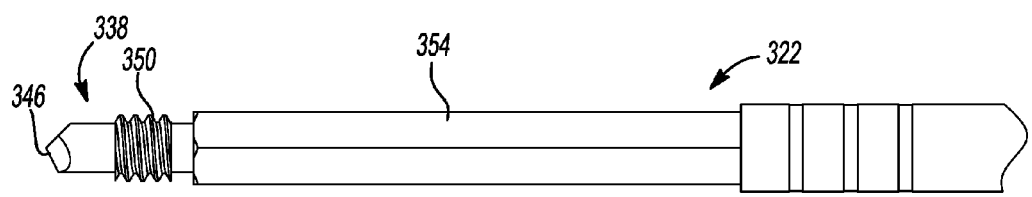

As can be seen in FIG. 8B, second end 342 can include a cutting portion 362 having a standard flute that extends partially toward first end 338 to a second hexagon portion 366. The second hexagon portion 366 can include a smaller diameter than the cutting portion 362, but the same as a third hexagon portion 368, thereby forming a shoulder 370 between the two portions. An annular recess 374 can be positioned between the second hexagon portion 366 and the third hexagon portion 368, as also shown in FIG. 8B. As will be discussed in greater detail below, second end 342 can be configured to both drill a bore in femur 14 as well as receive a drive collar over the cutting portion 362 to drive drill bit 322 to cut a pocket in tibia 18.

As briefly discussed above, first end 338 is configured to receive a quick-release driver 382 about first hexagon portion 354 for coupling drill bit 322 to a driving member to drill a bore 386 in the femur, as shown in FIG. 8. As can be seen in FIG. 8, drill bit 322 can exit femur 14 extra-articularly. In this regard, forming bores 226, 272 having longitudinal axes that are 30-40 degrees posterior to the longitudinal axis 66 of femur 14 along with the 45 degree angle of drill guide 290 can cooperate together to strategically position an exit of the drill bit 322 proximate an interior edge of the articular cartilage so as to not exit too deep into adjacent muscle tissue or out of condyle surface 26, as also shown in FIG. 8.

Once bore 386 has been formed in femur 14 as discussed above, quick-release driver 382 can be removed from drill bit 322 and drill guide 290 can then be removed from femur 14 by sliding drill guide about drill bit 322. In this regard, angled portion 328 can facilitate sliding the lower projection 328 out of bore 226 along the forty-five degree angle of drill bit 322 relative to the longitudinal axes of bores 226, 272. Drill bit 322 can then be slidably advanced to a position where first end 338 is proximate the joint space 390 between femur 14 and tibia 18, as shown in FIG. 9. A cannulated drill stop member 400 can be slidably received over drill 322 via second end 342 while drill bit 322 remains in femur 14. Drill stop member 400 can be advanced relative to drill bit 322 until a distal end 404 engages femur 14, as also shown in FIG. 9. A stop collar 412 can then be slidably received on drill bit 322 and can be positioned relative to a proximal end 416 of stop member 400 in preparation for final positioning, as will be discussed below. Stop collar 412 can be any appropriate device that can be fixed in various positions relative to bit 322. In the exemplary configuration shown in FIG. 9, stop collar 412 includes a cannulated longitudinal member 424 and a fastener 428 threadably engaged with member 424. As can be appreciated by one of ordinary skill in the art, fastener 428 can be tightened relative to member 424 so as to advance the fastener into fixed engagement with drill bit 322 and thus maintain collar 412 in a desired position relative to drill bit 322.

Figure 10:
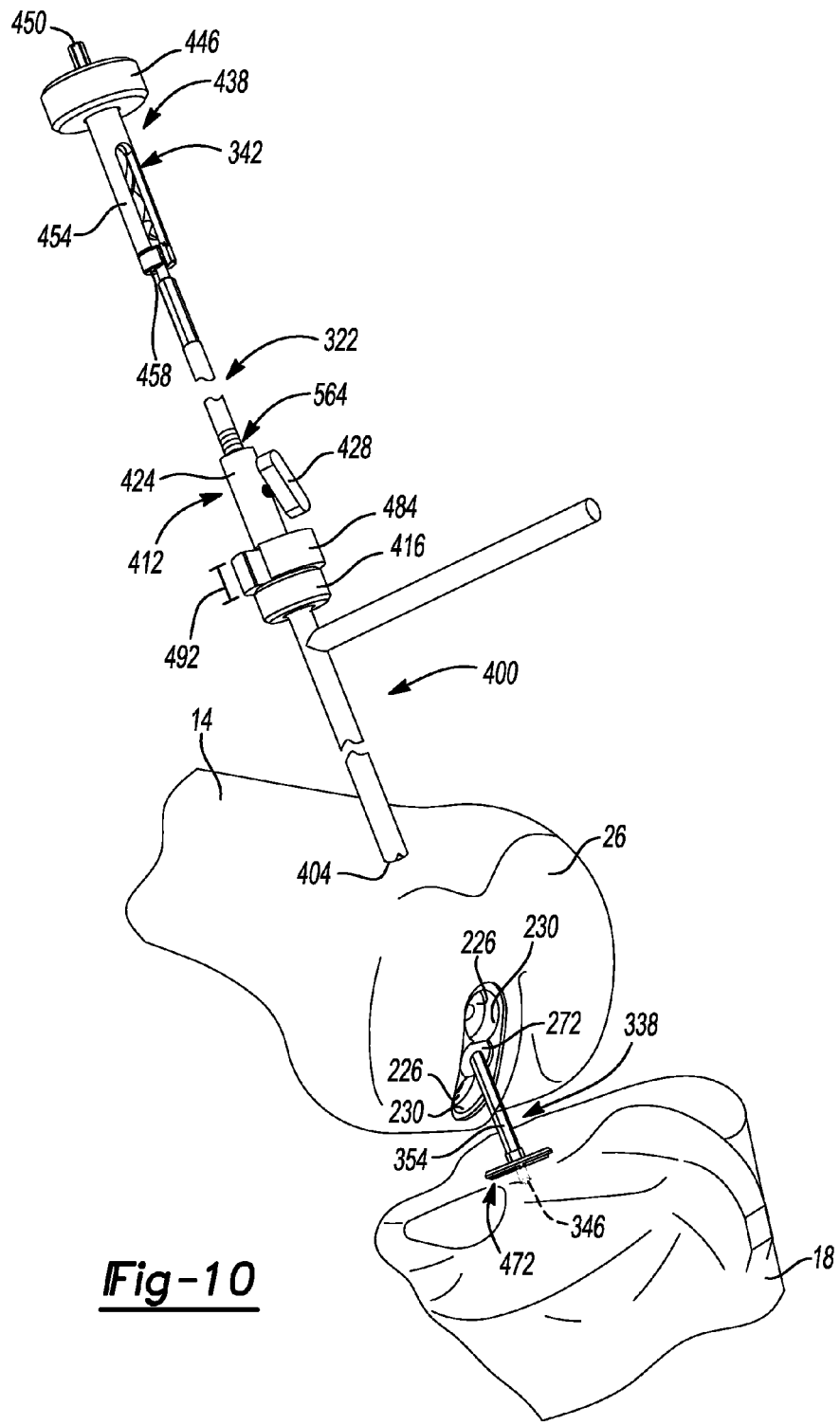
Figure 11:
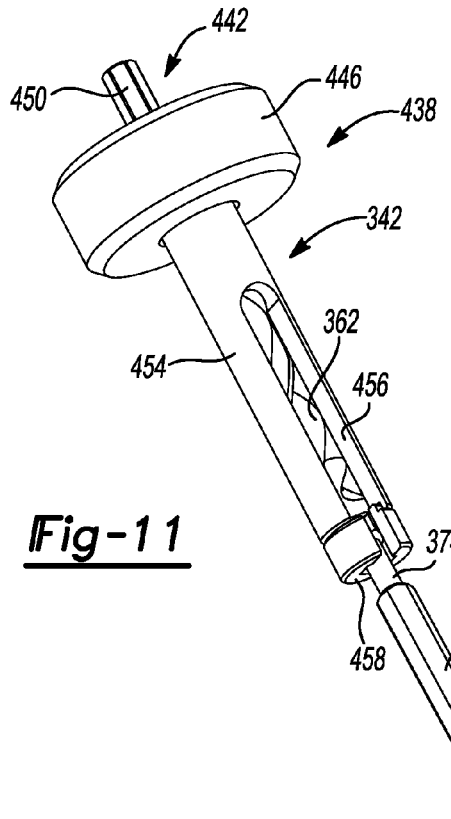
FIG. 11 is an enlarged view of the drill bit of FIG. 10 illustrating a drive collar in accordance with the teachings of the present disclosure.
Figure 11A:
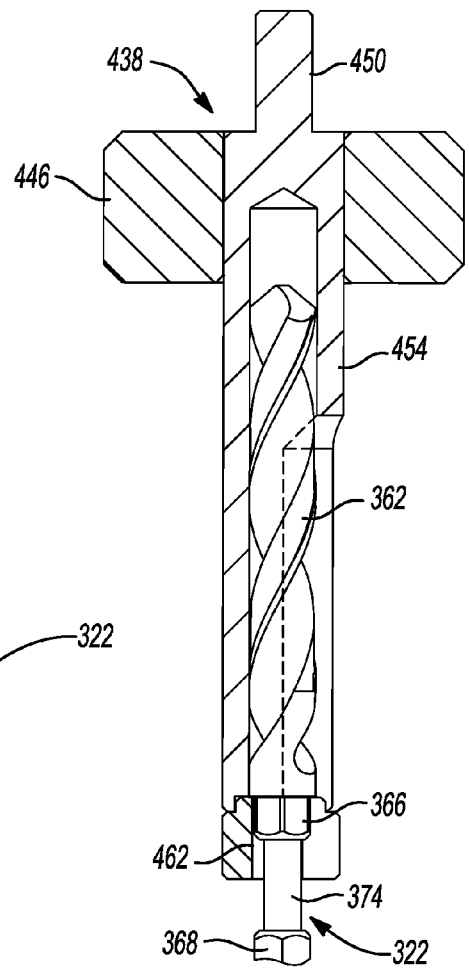
FIG. 11A is a sectional view of the drive collar of FIG. 11 in accordance with the teachings of the present disclosure.

Once stop collar 412 has been positioned on drill bit 322 as discussed above, a drive collar 438 can be positioned over second end 342 of drill bit 322, as shown in FIG. 10 with reference to FIGS. 11 and 11A. Drive collar 438 can include a first or proximal end 442 having a collar portion 446 and a hex drive protrusion 450. A cannulated portion 454 can extend from drive collar 438 up to and define a second or distal end 458. The distal end 458 can include an inner drive wall having a hexagon shape 462, as shown in FIG. 11A. Cannulated portion 454 can include a predetermined length correlated to a length of the cutting portion 362 of drill bit 322 such that the hexagon shaped drive wall 462 can engage the third hexagon portion 368 when drive collar 438 is urged toward femur 14, or can engage a second hexagon portion 366 when drive collar 438 is pulled away from femur 14, as shown in FIG. 11A. Drive collar 438 can be pivoted onto drill bit 322 via annular recess 374 and cut-out 456. The distal end 458 can be positioned over annular recess 374 via cut-out 456 shown in FIG. 11. Engagement of the distal end 458 of drive collar 438 with annular recess 374 can prevent drive collar 438 from coming off of drill bit 322 during extraction. In addition to serving a driving function, as will be discussed in greater detail below, drive collar 438 can also serve to protect a surgeon, clinician or other personnel from the cutting portion 362 of drill bit during the surgical procedure.

Figure 9A:
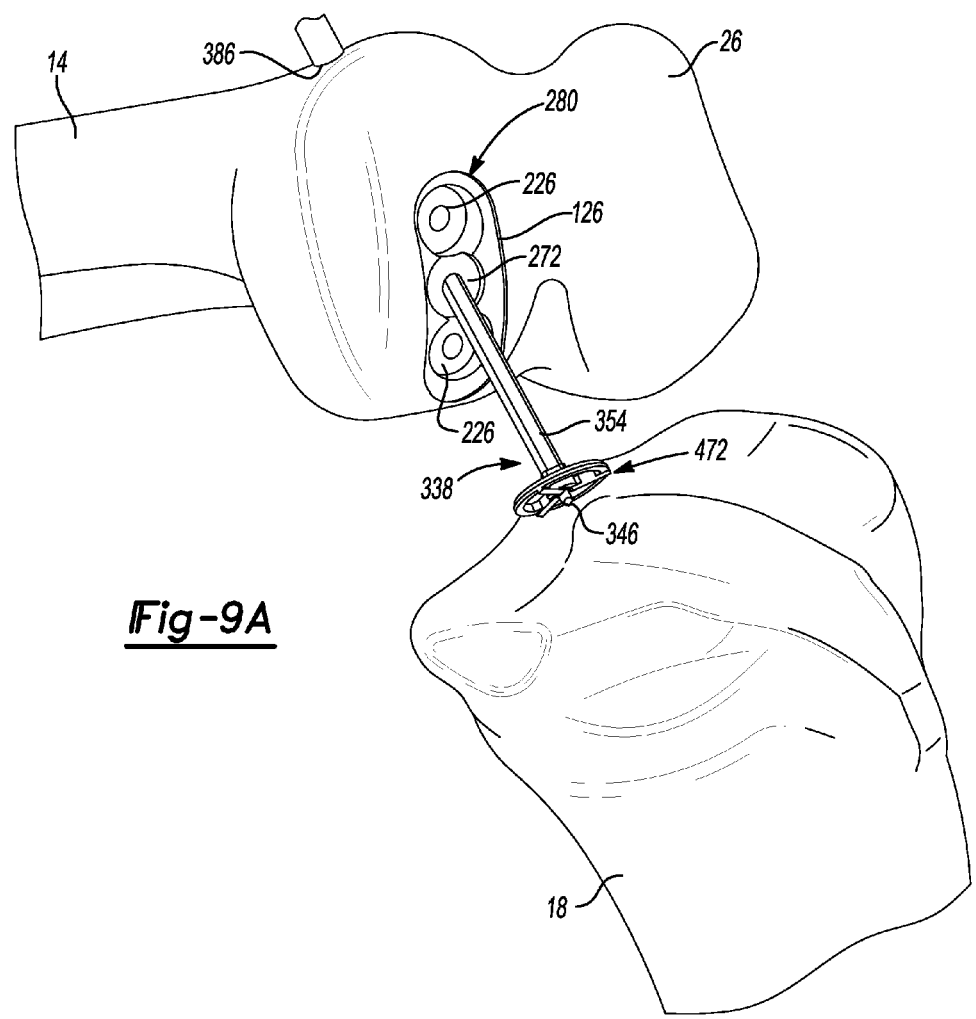

A cutter 472 can be threadably received on threaded portion 350 of bit 322 for use in cutting a pocket in tibia 18, as shown in FIGS. 9A and 10. In one exemplary aspect, drive collar 438 can be used to rotate drill bit 322 via collar portion 446 to threadably engage cutter 472 via internal female threads 476, as generally shown in FIG. 10. Pointed tip portion 346 of first end 338 can extend axially beyond cutter 472 to aid cutter 472 in initially engaging and cutting tibia 18, as shown for example in FIG. 9A. Once cutter 472 is coupled to drill bit 322, the drill bit 322 can be slidably advanced relative to femur 14 until cutter 472 contacts tibia 18. At this point, a spacer 484 can be received on drill bit 322 between proximal end 416 of drill stop member 400 and stop collar 412. In one exemplary aspect, a longitudinal or axial thickness 492 of spacer 484 can correspond to a depth of a pocket cut into tibia 18 by cutter 472, as will be discussed in greater detail below.

Figure 12:
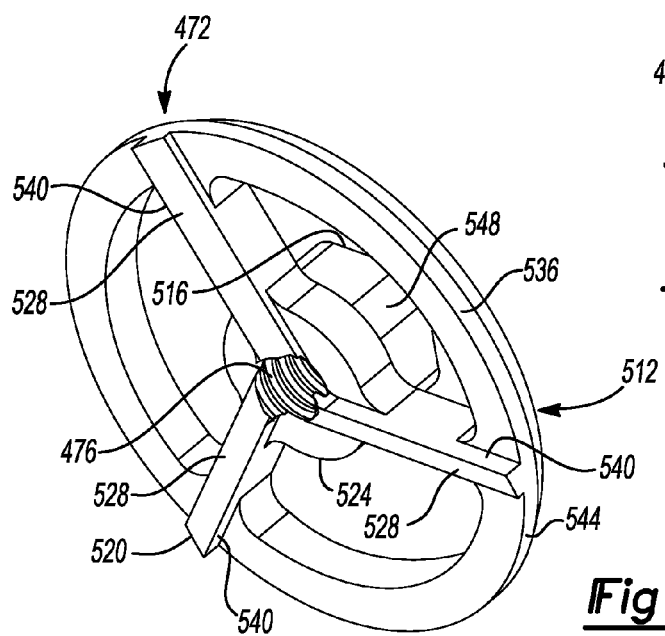
FIG. 12 is a perspective view of a tibial cutter of FIG. 12 in accordance with the teachings of the present disclosure.

Cutter 472 can include a body 512 having a first or proximal end 516 and an opposite second bone engaging end 520, as shown in FIG. 12. Body 512 can define a central hub 524 and a plurality of cutting members 528, such as the three cutting members 528 illustrated in FIG. 12, that extend radially outward from hub 524 to an annular ring 536. Each cutting member 528 can include a cutting blade or edge 540 on a distal surface thereof, as also shown in FIG. 12. In one exemplary aspect, the cutting blades 540 can extend radially outward to a radially outermost edge 544 of cutter 472. Central hub 524 can define an internal bore having threads 476 configured to threadably receive threaded portion 350 of bit 322 in the manner discussed above. An outer wall of hub 524 adjacent the proximal end 516 can include a square shape 548 configured to receive a tool (not shown) to aid in securing cutter 472 to drill bit 322.

Figure 14:
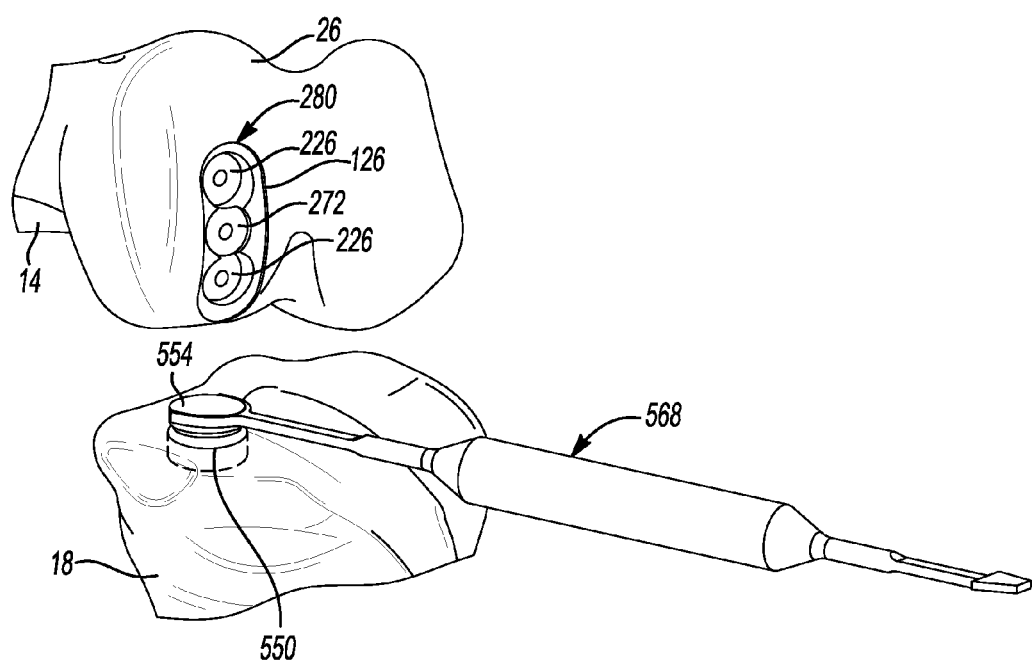
FIG. 14 is a perspective view of the exemplary procedure depicting positioning a tibial bearing implant relative to the tibial pocket with an instrument in accordance with the teachings of the present disclosure.

Once spacer 484 is positioned on drill bit 322 as discussed above, one side of spacer 484 can be brought into contact with proximal end 416 and stop collar 412 can be brought into contact with an opposite side of spacer 484, as shown in FIG. 10. The tibia can be rotated so that cutter 472 is perpendicular to a tibial plateau of the tibia. At this point, the distal end 404 of drill stop member 400 should be contacting femur 14, and cutter 472 should be in contact with tibia 18 at the location for the implant. Fastener 428 can be tightened to secure stop collar 412 in this position, after which spacer 484 can be removed. A drill driving member (not shown), such as the driving member discussed above, can be coupled to hex drive protrusion 450 of drive collar 438 for driving drill bit 322 and cutter 472 to cut a pocket in tibia 18. In particular, drill bit 322 and cutter 472 can be advanced relative to femur 14 and drill stop member 400 to cut a pocket 550 (FIG. 14) in tibia 18 for receipt of a tibial bearing implant 554 (FIG. 14). Tip portion 346 of drill bit 322 can initially engage tibia 18 to assist in cutting pocket 550. Drill bit 322 can be advanced to cut pocket 550 with cutter 472 until stop collar 412 engages the proximal end 416 of drill stop member 400 thereby limiting the depth of pocket 550 to a predetermined depth corresponding to tibial bearing 554.

Pocket 550 can be formed to remove a corresponding lesion or defect in tibia 18. In this regard, cutter 472 can be provided in various sizes, such as various diameters, to account for varying sizes of the tibial defect. Tibial bearing 554 can similarly be provided in various diameter sizes corresponding to the various sizes of cutter 472.

Once pocket 550 has been formed in tibia 18, a trial tibial bearing 562 (FIG. 13C) can be positioned in pocket 550 in a similar manner as tibial implant 554 is shown in FIG. 14 being positioned in pocket 550. An exemplary instrument 568 can be used to position both trial bearing 562 and bearing implant 554 in pocket 550, as will be discussed below. If the tibial pocket 550 is determined not to be deep enough based on an evaluation of the trial bearing placement in pocket 550, cutter 472 can be used to form pocket 550 deeper into tibia 18. In this regard, stop collar 412 can be loosened from drill bit 322 and depth marking indicia 564 (FIG. 10) on drill bit 322 can be used as reference marks in forming pocket 550 deeper into tibia 18.

Figure 13:
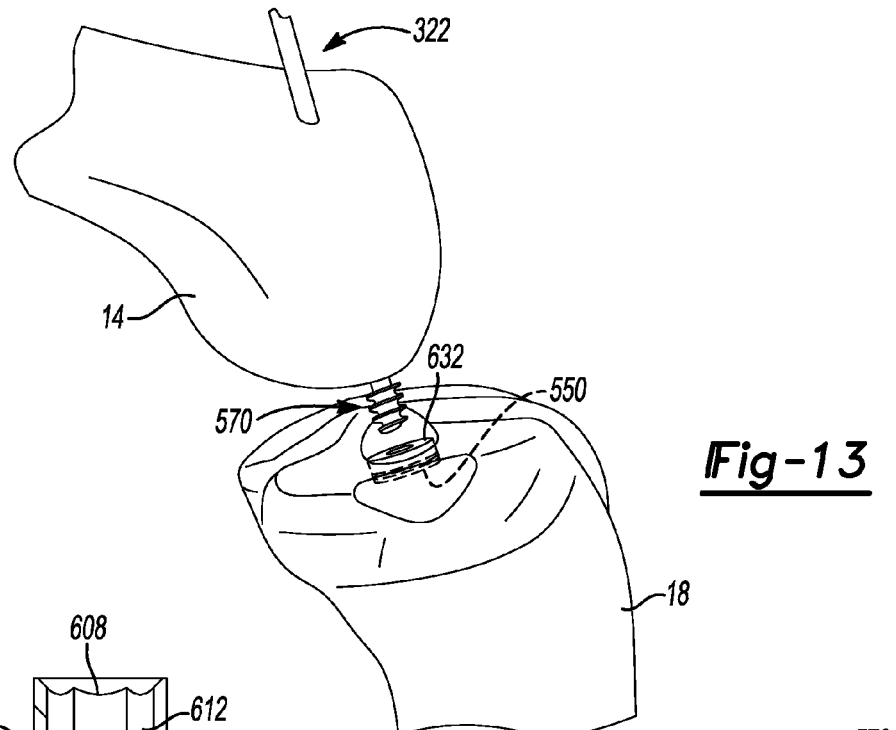
FIG. 13 is a perspective view of the exemplary procedure depicting an exemplary tibial screw implant coupled to the drill bit for optional implantation relative to the tibial pocket in accordance with the teachings of the present disclosure.
Figure 13A:
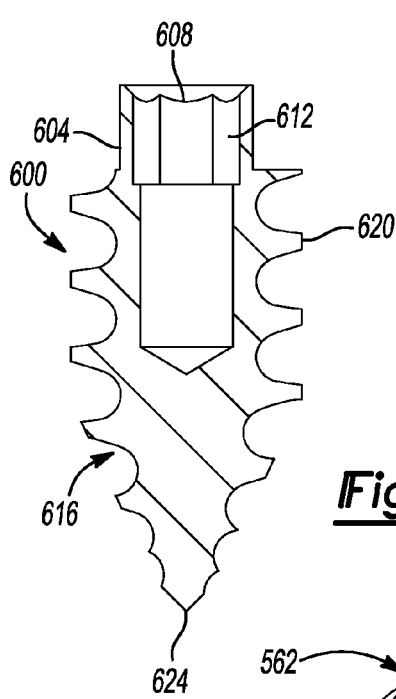
FIG. 13A is a partial sectional view of a tibial screw implant tap in accordance with the teachings of the present disclosure.
Figure 13B:
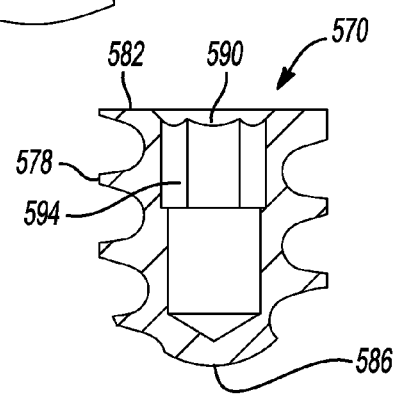
FIG. 13B is a partial sectional view of the tibial screw implant of FIG. 13 in accordance with the teachings of the present disclosure.
Figure 13C:
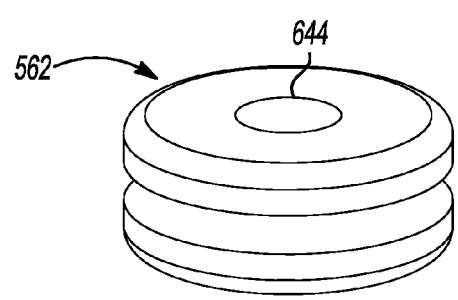
FIG. 13C is a perspective view of a trial tibial bearing in accordance with the teachings of the present disclosure.

On the other hand, if it is determined that pocket 550 has been formed too deep into tibia 18 and/or the sub-cortical bone is too soft, a tibial adjustment screw 570 can be implanted into pocket 550, as generally shown in FIG. 13. Optional tibial adjustment screw 570 can be used to provide structural support for tibial bearing 554 and/or to adjust the depth of pocket 550, as will be discussed in greater detail below. Referencing FIG. 13B, tibial adjustment screw 570 can include external threads 578 extending from a proximal end 582 to a distal end 586. Proximal end 582 can include an internal blind bore 590 having a hexagonal shape 594 complimentary to the first hexagonal shaped portion 354 of bit 322. In this regard, cutter 472 can be removed from bit 322 and tibial adjustment screw 570 can be positioned about the first end of bit 322 such that the first hexagonal portion 354 engages the hexagonal shape 594 of tibial screw bore 590. Drill bit 322 can then be used to drive tibial adjustment screw 570 into pocket 550, as will be discussed below in greater detail.

Before tibial adjustment screw 570 is coupled to drill bit 322 and implanted into pocket 550, an optional tibial adjustment screw tap 600 (FIG. 13A) can be used to tap tibia 18 for receipt of screw 570 discussed above. The tibial adjustment screw tap 600 can include a substantially similar structure and can couple to drill bit 322 in the same manner as screw 570 and thus will not be described in detail herein. Briefly, however, screw tap 600 can include a proximal end 604, an internal blind bore 608 having a hexagonal shaped sidewall 612, and a conical shape 616 with external threads 620 extending to a distal tip 624.

A screw and tap guide ring 632 can be used to guide both the tap 600 and/or the screw 570, as discussed below and shown in FIG. 13. In particular, guide ring 632 can include an outer diameter complementary to an inner diameter of pocket 550 such that guide ring can be snugly positioned within pocket 550. Guide ring 632 can also include a central throughbore 636 sized and shaped to receive the tap 600 and/or bearing screw 570 therethrough. It should be understood that guide ring 632 is optional. In an exemplary aspect, guide ring 632 is removed after implantation of tibial screw 570 and before implanting tibial bearing 554 in pocket 550. It should also be understood that both the tap 600 and screw 570 can be coupled to drill bit 322 without having to remove the drill bit from femur 14.

With screw tap 600 coupled to drill bit 322 in the manner discussed above, tibia 18 can be tapped in a central location of pocket 550 using optional guide ring 632 as a guide. The tap 600 can be threaded into tibia 18 until a proximal end of the threads is flush with a bottom of pocket 550. In one exemplary aspect, drive collar 438 can be used to rotate drill bit 322 instead of the drive member to perform the tapping and implanting operation associated with screw 570. The tap 600 can then be removed from drill bit 322 and tibial screw 570 can be coupled to bit 322 in the manner discussed above. Tibial screw 570 can be threaded into the tapped threads in tibia 18 using drive collar 438. The guide ring 632 can be optionally removed before implanting screw 570, as discussed above. Screw 570 can be provided in various sizes, such as various lengths and diameters. Tap 600 can therefore also be provided in various sizes corresponding to the various sizes of screw 570. The guide ring 632 can also be provided with various through bore sizes.

First end 338 of drill bit 322 can then be slidably removed from screw 570 and the trial bearing 562 can again be positioned in pocket 550 to check the fit of the trial bearing 562. If it is determined that the trial bearing 562 needs to be raised toward the articular surface of the tibia 18 (i.e., toward femur 14), then first end 338 can be inserted through a central throughbore 644 of the trial bearing 562 and into engagement with screw 570. Drill bit 322 can then be rotated in an appropriate direction to raise the trial bearing 562 to an appropriate position. In this regard, it should be appreciated that the diameter of through bore 644 is large enough to allow drill bit 322 to pass through, but smaller in diameter than screw 570 so that the trial bearing 562 can be raised or lowered when screw 570 is turned. Once screw 570 is adjusted to place the trial bearing 562 in the appropriate position, drill bit 322 can be removed from femur 14 along with the associated stop collar 412, drive collar 438 and drill stop member 400.

Before implanting the femoral and tibial implants 30, 554, a femoral trial (not shown) can be positioned in the femoral pocket 280 and the trial bearing 562 can remain removably positioned in tibia 18. The femoral trial can be substantially similar to femoral implant 30 shown in FIG. 16A such that the femoral trial will not be discussed in further detail herein. With the femoral and tibial trials in place, the leg can be articulated to check for a smooth transition between the respective trials and surrounding articular cartilage.

The femoral and tibial trials can then be removed and the femoral and tibial pockets 280, 550 can be prepared for receipt of respective implants 30, 554. In one exemplary aspect, bone cement can be used to secure the implants 30, 554 to the respective pockets 280, 550. In this aspect, bone cement can be applied to one or both of the bottom of pocket 550 and the bottom of tibial bearing 554. Instrument 568 can then be used to position tibial bearing 554 into pocket 550, as shown in FIG. 14. Once tibial bearing 554 is placed in pocket 550, a tibial bearing impactor 652 (FIG. 15) can be used to seat bearing 554 into pocket 550 and, if previously implanted, against bearing screw 570.

Figures 15, 15A:
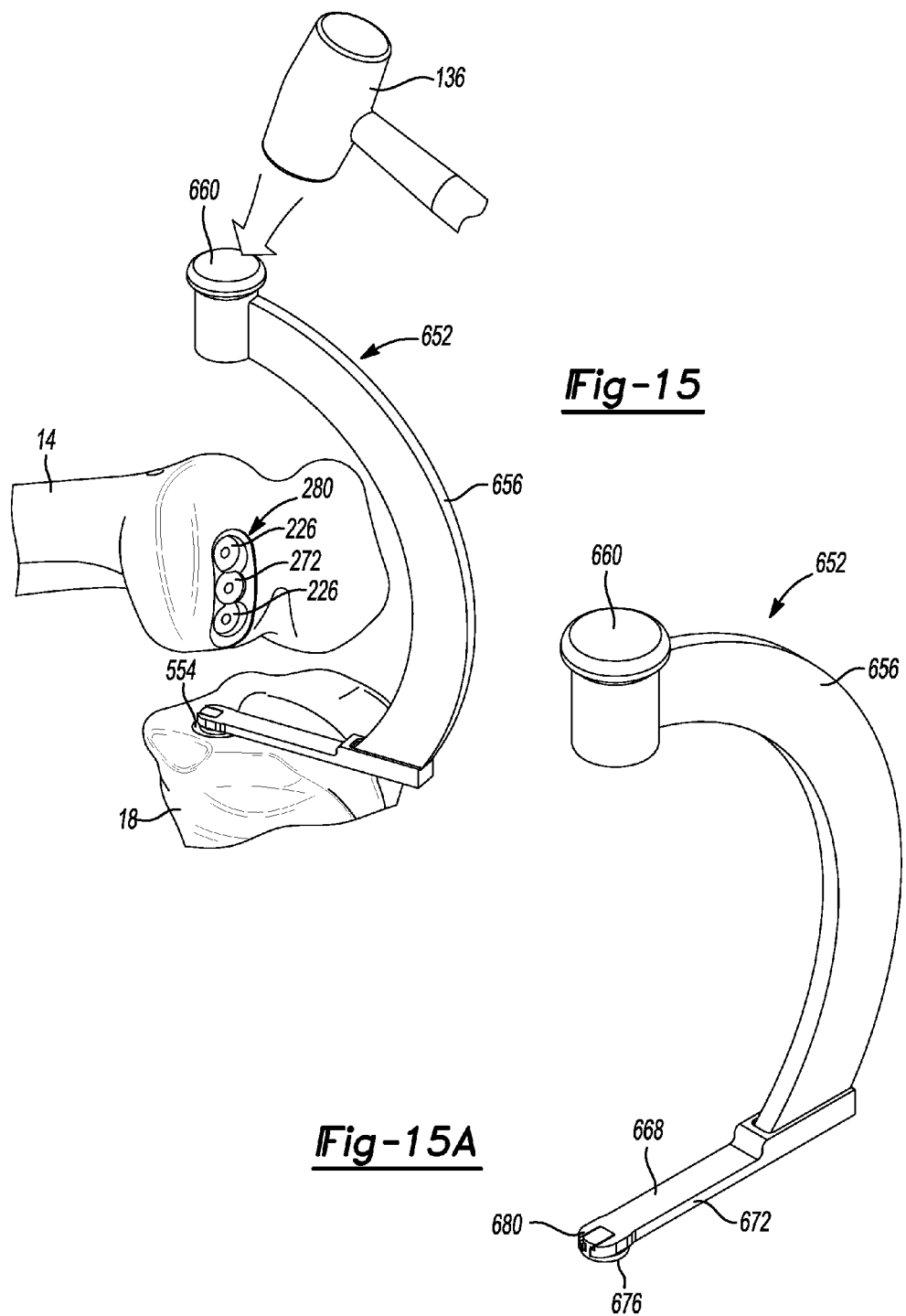
FIG. 15 is a perspective view of the exemplary procedure depicting seating the tibial bearing implant relative to the tibial pocket with a tibial bearing impactor in accordance with the teachings of the present disclosure.
FIG. 15A is a perspective view of the tibial bearing impactor of FIG. 15 in accordance with the teachings of the present disclosure.

As can be seen in FIG. 15A, tibial bearing impactor 652 can have a generally C-shaped body 656 so as to fit around femur 14. Body 656 can include a first impact receiving end 660 configured to be impacted with impact member 136, and an opposite bearing engaging end 668. Bearing engaging end 668 can include a linear portion 672 having a protrusion 676 at a free end 680 configured to engage bearing 554, as shown in FIGS. 15 and 15A.

With additional reference to FIGS. 16 and 16A, preparation for and implantation of femoral implant 30 will now be discussed. Femoral implant 30 can be provided with a variety of outer perimeter 48 sizes and can include a femoral pocket engaging side 692 and an opposite articulation side 696. Bone engaging side can include the outer projections 234 corresponding to outer bores 226 and the inner projection 276 corresponding to inner bore 272, as shown in FIG. 16A. The outer perimeter 48 of each implant 30 can be sized and shaped to correspond with outline 126 cut in the femoral articular cartilage with cartilage cutter 100 discussed above. In one exemplary configuration, the outer perimeter 48 can vary in size to correspond with the outline 126 while the outer and inner projections 234, 276 remain the same among the implants 30.

In the exemplary aspect where bone cement can be used as a securing method, bone cement can similarly be applied to the pocket engaging side 692 of femoral implant 30 and a bottom of bores 226, 272 of pocket 280. Implant 30 can then be positioned in femoral pocket 280 such that outer projections 234 are received in outer bores 226 and inner projection 276 is received in inner bore 272, as shown in FIG. 16 with reference to FIG. 15. Implant 30 can then be seated in pocket 280 using a femoral impactor 702 and impact member 136, as also shown in FIG. 16.

Figure 17:
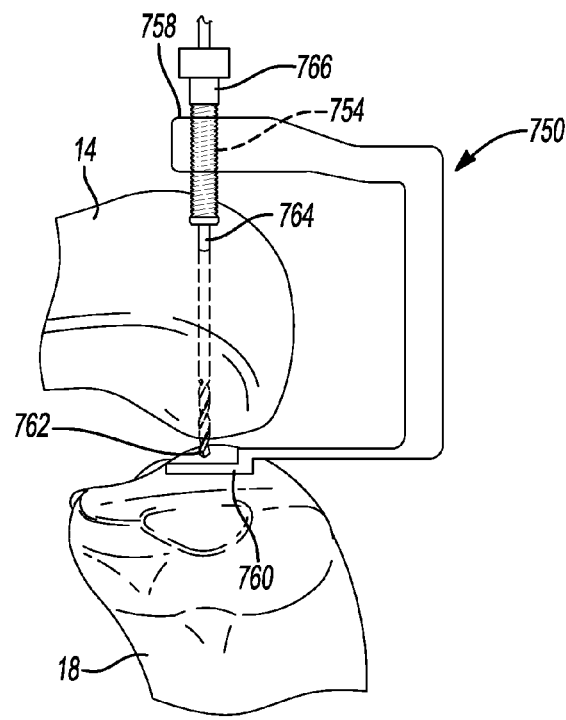
FIGS. 17-19 are perspective views of another exemplary procedure depicting forming a tibial pocket using a bore in the femur in accordance with the present teachings.

With additional reference to FIGS. 17-19, an alternative method and system for forming tibial pocket 550 will now be discussed, where like reference numerals refer to like features previously introduced and discussed. A substantially C-shaped guide member 750 can be positioned as shown in FIG. 17 to extend around the condyle area of femur 14. Guide member 750 can include a threaded bore 754 at a first or upper end 758 and a second opposite end 760 configured to rest on tibia 18 and receive a distal end 762 of drilling member 764, as shown for example in FIG. 17. Threaded bore 754 can threadably receive a cannulated bullet 766 therethrough.

Bullet 766 can be threadably advanced until it engages femur 14 to secure bullet 766 and guide relative to femur 14, as also shown in FIG. 17. Drilling member 764 can then be inserted through cannulated bullet 766 and rotated with a driving member (not shown) to drill a bore 770 though femur 14. Drilling member 764 can be advanced relative to femur 14 until distal end 762 engages second end 760.

Figures 18, 19:
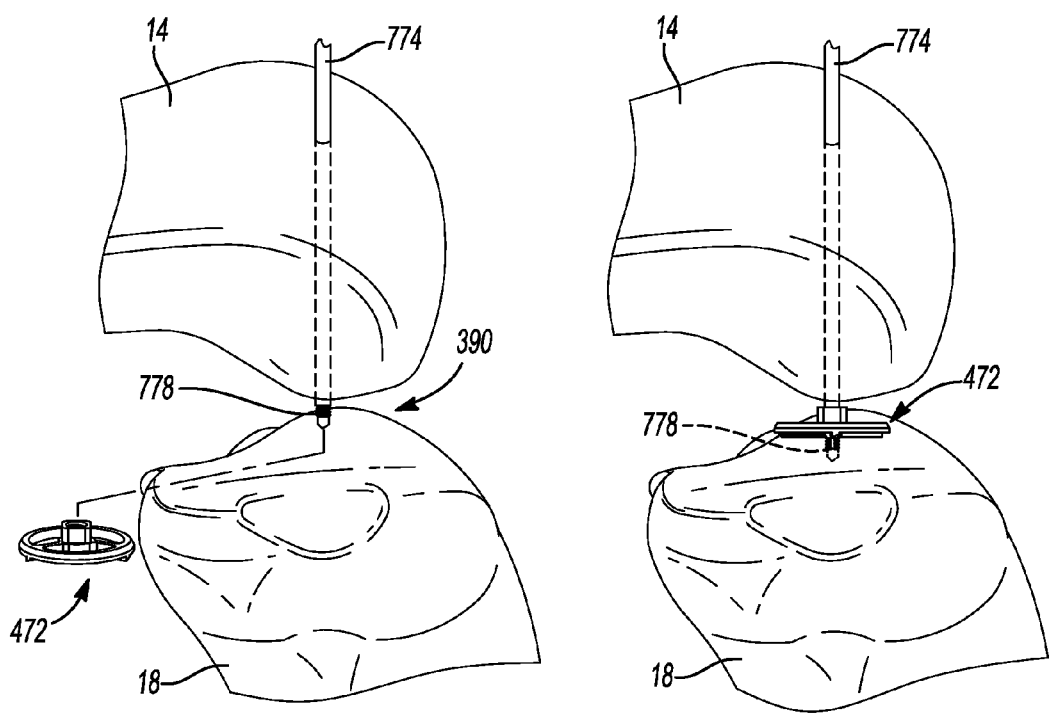

With particular reference to FIGS. 18 and 19, drilling member 764 can be removed from bullet 766 and the bullet can be disengaged from femur 14 so as to provide for removal of guide member 750 from the anatomy. A drive shaft 774 can then be slidably inserted through bore 770 until a threaded distal end 778 is positioned relative to joint space 390. Cutter 472 can then be threadably engaged to distal end 778 in the same manner as discussed above in connection with drill bit 322. Drive shaft 774 can be rotated with any suitable drive member to form pocket 550 in tibia 18, as generally shown in FIG. 19 with reference to pocket 550 of FIG. 14. The trial bearing 562, screw 570 and/or tap 600 can then be used in a similar manner as discussed above to check the fit of pocket 550. Tibial bearing 554 can then be implanted using the technique and instruments discussed above.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A system for use in repairing a soft tissue or bone defect, comprising:
   a C-shaped guide member having a first end and a second end and configured to extend around a condyle area of a femur of a patient, the guide member including a threaded bore at the first end, the second end configured to rest on a tibia of the patient;
   a cannulated bullet threadably received in the threaded bore and configured to be threadably advanced to secure the guide member relative to the femur;
   a drilling member insertable through the bullet and configured to drill a femoral bore through the femur; and
   a drive shaft configured to be slidably inserted through the femoral bore after the guide member and the drilling member are removed, the drive shaft having a cutter on a distal end and configured to form a pocket in the tibia with the drive shaft extending through the femoral bore.

2. The system of claim 1 wherein the drive shaft includes a threaded distal end configured to be positioned in a joint space between the femur and the tibia.

3. The system of claim 2, wherein the cutter is configured to be threadably received on the threaded distal end of the drive shaft and configured to form the pocket in the tibia relative to the defect.

4. The system of claim 3, wherein the cutter includes a body having a first end and an opposite second bone-engaging end, the body defining a central hub and a plurality of cutting members extending radially from the central hub.

5. The system of claim 4, wherein the central hub defines an internal threaded bore configured to be threadably coupled to the threaded distal end of the drive shaft.

6. The system of claim 4, wherein the cutting members form an annular ring.

7. The system of claim 6, wherein each cutting member includes a cutting blade extending from the central hub to the annular ring.

8. A system for use in repairing a soft tissue or bone defect, comprising:
   a C-shaped guide member having a first end and a second end and configured to extend around a condyle area of a femur of a patient, the guide member including a threaded bore at the first end, the second end configured to rest on a tibia of the patient;
   a cannulated bullet threadably received in the threaded bore and configured to be threadably advanced to secure the guide member relative to the femur;
   a drilling member insertable through the bullet and configured to drill a femoral bore through the femur;
   a drive shaft configured to be slidably inserted through the femoral bore after the guide member and the drilling member are removed, the drive shaft having a threaded distal end configured to be positioned in a joint space between the femur and the tibia; and
   a cutter configured to be threadably received on the threaded distal end of the drive shaft and configured to form a pocket in the tibia relative to the defect wherein the cutter includes a body having a first end and an opposite second bone-engaging end, the body defining a central hub and a plurality of cutting members extending radially from the central hub, wherein the central hub has an outer wall adjacent to the first end, the outer wall including a square shape configured to receive a tool for securing the cutter to the drive shaft.

9. The system of claim 8, further comprising a trial tibial bearing configured to be positioned in the pocket for depth evaluation.

10. The system of claim 9, further comprising a tibial adjustment screw configured to be implanted in the pocket using the drive shaft after the cutter is removed.

11. A system for use in repairing a soft tissue or bone defect, comprising:
    a C-shaped guide member having a first end and a second end and configured to extend around a condyle area of a femur of a patient, the guide member including a threaded bore at the first end, the second end configured to rest on a tibia of the patient;

a cannulated bullet threadably received in the threaded bore and configured to be threadably advanced to secure the guide member relative to the femur;

a drilling member insertable through the bullet and configured to drill a femoral bore through the femur;

a drive shaft configured to be slidably inserted through the femoral bore after the guide member and the drilling member are removed, the drive shaft having a threaded distal end configured to be positioned in a joint space between the femur and the tibia; and a cutter configured to be threadably received on the threaded distal end of the drive shaft and configured to form a pocket in the tibia relative to the defect, wherein the pocket is formed in the tibia by the cutter with the drive shaft extending through the femur.

12. The system of claim 11, wherein the cutter includes a body having a first end and an opposite second bone-engaging end, the body defining a central hub and a plurality of cutting members extending radially from the central hub.

13. The system of claim 12, wherein the central hub defines an internal threaded bore configured to be threadably coupled to the threaded distal end of the drive shaft.

14. The system of claim 12, wherein the cutting members form an annular ring.

15. The system of claim 14, wherein each cutting member includes a cutting blade extending from the central hub to the annular ring.

16. A system for use in repairing a soft tissue or bone defect, comprising:

a guide member having a first end and a second end configured to extend around a distal end of a femur of a patient, the guide member including a bore at the first end and the second end configured to rest on a tibia of the patient;

a cannulated bullet axially received in the bore and configured to be axially advanced to secure the guide member relative to the femur for use in guiding a formation of a femoral bore through the femur;

a drive shaft configured to be slidably inserted through the femoral bore, the drive shaft having a distal end configured to be positioned in a joint space between the femur and the tibia; and a cutter configured to be coupled on the distal end of the drive shaft and configured to form a pocket in the tibia relative to the defect, wherein the pocket is formed in the tibia by the cutter with the drive shaft extending through the femur.

17. The system of claim 16, further comprising a drilling member insertable through the bullet and configured to drill the femoral bore through the femur.

18. The system of claim 16, wherein the guide member is C-shaped and configured to extend around a condyle area of the distal end of the femur.

19. The system of claim 16, wherein the bore at the first end of the guide member is threaded and the cannulated bullet is threaded and configured to be threadably received in the threaded bore.

20. The system of claim 16, wherein the distal end of the drive shaft is threaded and the cutter is configured to be threadably received on the threaded distal end of the drive shaft.

* * * * *